(12) United States Patent
Saris et al.

(10) Patent No.: US 7,892,733 B1
(45) Date of Patent: Feb. 22, 2011

(54) RESPONSE ELEMENT REGIONS

(75) Inventors: Christiaan J. M. Saris, Newbury Park, CA (US); Shamin Summer, Oak Park, CA (US); Sharon X. Mu, Thousand Oaks, CA (US); Jill A. Crouse, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 1457 days.

(21) Appl. No.: 11/112,973

(22) Filed: Apr. 22, 2005

Related U.S. Application Data

(60) Provisional application No. 60/564,724, filed on Apr. 22, 2004, provisional application No. 60/565,135, filed on Apr. 23, 2004.

(51) Int. Cl.
*C12Q 1/02* (2006.01)
*C12Q 1/66* (2006.01)
*C12Q 1/68* (2006.01)
*C12P 21/00* (2006.01)
*C12N 15/00* (2006.01)
*C12N 15/09* (2006.01)
*C07H 21/04* (2006.01)

(52) U.S. Cl. .............. 435/6; 435/8; 435/29; 435/69.1; 435/70.1; 435/320.1; 536/24.1

(58) Field of Classification Search ............ None
See application file for complete search history.

(56) References Cited

U.S. PATENT DOCUMENTS

| | | |
|---|---|---|
| 5,616,489 A | 4/1997 | Levy et al. |
| 5,648,217 A | 7/1997 | Levy et al. |
| 5,707,803 A | 1/1998 | Lamb et al. |
| 5,712,094 A | 1/1998 | Seidel et al. |
| 5,814,517 A | 9/1998 | Seidel et al. |
| 6,171,864 B1 | 1/2001 | Coughlan et al. |
| 6,541,244 B1 | 4/2003 | Auernhammer et al. |
| 6,573,068 B1 | 6/2003 | Edwards et al. |
| 2003/0077591 A1 | 4/2003 | Denefle et al. |

FOREIGN PATENT DOCUMENTS

| | | |
|---|---|---|
| EP | 1 104 808 A1 | 6/2001 |
| WO | WO 99/53051 A2 | 10/1999 |
| WO | WO 00/06696 A2 | 2/2000 |
| WO | WO 00/37491 A2 | 6/2000 |
| WO | WO 00/75326 A1 | 12/2000 |
| WO | WO 01/00806 A2 | 1/2001 |
| WO | WO 02/22654 A1 | 3/2002 |
| WO | WO 03/018803 A1 | 3/2003 |

OTHER PUBLICATIONS

Alam and Cook. "Reporter genes for monitoring gene expression in mammalian cells." Gene Transfer and Expression in Mammalian Cells. Ed. S.C. Makrides. Esevier Science B.V., 2003. 291-308.*
Yamada et al. Characterization and purification of carbohydrate response element-binding protein of the rat L-type pyruvate kinase gene promoter. Biochemical and Biophysical Research Communications, vol. 257, pp. 44-49, 1999.*
Decker et al., "GAS elements: a few nucleotiodes with a major impact on cytokine-induced gene expression," *J. Interferon Cytokine Res.* 17(3):121-34 (1997).
Genbank Accession No. BN000945 (Nov. 14, 2006).
Gilmour et al., "Interleukin 2 activates STAT5 transcription factor (mammary gland factor) and specific gene expression in T lymphocytes," *Proc. Natl. Acad. Sci. USA* 92(23):10772-76 (1995).
Kanno et al., "The genomic structure of the murine ICSBP gene reveals the presence of the gamma interferon-responsive element, to which an ISGF3α subunit (or similar) molecule binds," *Mol. Cell. Biol.* 13(7), 3951-63 (1993).
Lécine et al., Elf-1 and Stat5 bind to a critical element in a new enhancer of the human interleukin-2 receptor a gene, *Mol. Cell. Biol.* 16(12):6829-40 (1996).
Rameil et al., "IL-2 and long-term T cell activation induce physical and functional interaction between STAT5 and ETS transcription factors in human T cells," *Oncogene* 19:2086-97 (2000).
Sherman et al., "Role of signal transduction and activators of transcription 1 and -3 in inducible regulation of the human angiotensinogen gene by interleukin-6," *Mol. Endocrinol.* 15(3):441-57 (2001).
Tessitore et al., "Two y-interferon-activation sites (GAS) on the promoter of the human intercellular adhesion molecule (ICAM-1) gene are required for induction of transcription by IFN-γ," *Eur. J. Biochem.* 258(3):968-75 (1998).

\* cited by examiner

*Primary Examiner*—Jennifer Dunston
(74) *Attorney, Agent, or Firm*—Michael G. Penn

(57) ABSTRACT

Response element regions, DNA constructs comprising response element regions, host cells comprising response element regions, and methods of using response element regions are provided.

55 Claims, 1 Drawing Sheet

```
                              SEQUENCE LISTING

<160> NUMBER OF SEQ ID NOS: 41

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtcatttcca ggaaatcacc                                                      20

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtcatttcca ggaaatcacc gtcatttcca ggaaatcacc gtcatttcca ggaaatcacc          60

<210> SEQ ID NO 3
<211> LENGTH: 143
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(83)
<223> OTHER INFORMATION: This region may encompass 0 to 23 variable
      nucleotide bases; a, c, g, or t

<400> SEQUENCE: 3
gtcatttcca ggaaatcacc gtcatttcca ggaaatcacc gtcatttcca ggaaatcacc          60
nnnnnnnnnn nnnnnnnnnn nnngtcattt ccaggaaatc accgtcattt ccaggaaatc         120
accgtcattt ccaggaaatc acc                                                143

<210> SEQ ID NO 4
<211> LENGTH: 226
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(83)
<223> OTHER INFORMATION: This region may encompass 0 to 23 variable
      nucleotide bases; a, c, g, or t
<220> FEATURE:
<221> NAME/KEY: modified_base
<222> LOCATION: (144)..(166)
<223> OTHER INFORMATION: This region may encompass 0 to 23 variable
      nucleotide bases; a, c, g, or t

<400> SEQUENCE: 4
gtcatttcca ggaaatcacc gtcatttcca ggaaatcacc gtcatttcca ggaaatcacc          60
nnnnnnnnnn nnnnnnnnnn nnngtcattt ccaggaaatc accgtcattt ccaggaaatc         120
accgtcattt ccaggaaatc accnnnnnnn nnnnnnnnnnn nnnnnngtca tttccaggaa        180
```

```
atcaccgtca tttccaggaa atcaccgtca tttccaggaa atcacc              226
```

<210> SEQ ID NO 5
<211> LENGTH: 309
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(83)
<223> OTHER INFORMATION: This region may encompass 0 to 23 variable
      nucleotide bases; a, c, g, or t
<220> FEATURE:
<221> NAME/KEY: modified_base
<222> LOCATION: (144)..(166)
<223> OTHER INFORMATION: This region may encompass 0 to 23 variable
      nucleotide bases; a, c, g, or t
<220> FEATURE:
<221> NAME/KEY: modified_base
<222> LOCATION: (227)..(249)
<223> OTHER INFORMATION: This region may encompass 0 to 23 variable
      nucleotide bases; a, c, g, or t

<400> SEQUENCE: 5

```
gtcatttcca ggaaatcacc gtcatttcca ggaaatcacc gtcatttcca ggaaatcacc    60
nnnnnnnnnn nnnnnnnnnn nnngtcattt ccaggaaatc accgtcattt ccaggaaatc   120
accgtcattt ccaggaaatc accnnnnnnn nnnnnnnnnn nnnnnngtca tttccaggaa   180
atcaccgtca tttccaggaa atcaccgtca tttccaggaa atcaccnnnn nnnnnnnnnn   240
nnnnnnnnng tcatttccag gaaatcaccg tcatttccag gaaatcaccg tcatttccag   300
gaaatcacc                                                         309
```

<210> SEQ ID NO 6
<211> LENGTH: 168
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(108)
<223> OTHER INFORMATION: This region may encompass 0 to 48 variable
      nucleotide bases; a, c, g, or t

<400> SEQUENCE: 6

```
gtcatttcca ggaaatcacc gtcatttcca ggaaatcacc gtcatttcca ggaaatcacc    60
nnnnnnnnnn nnnnnnnnnn nnnnnnnnnn nnnnnnnnnn nnnnnnnngt catttccagg   120
aaatcaccgt catttccagg aaatcaccgt catttccagg aaatcacc              168
```

<210> SEQ ID NO 7
<211> LENGTH: 276
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(108)
<223> OTHER INFORMATION: This region may encompass 0 to 48 variable
      nucleotide bases; a, c, g, or t
<220> FEATURE:
<221> NAME/KEY: modified_base
<222> LOCATION: (169)..(216)
<223> OTHER INFORMATION: This region may encompass 0 to 48 variable -continued nucleotide bases; a, c, g, or t

<400> SEQUENCE: 7
gtcatttcca ggaaatcacc gtcatttcca ggaaatcacc gtcatttcca ggaaatcacc        60
nnnnnnnnnn nnnnnnnnnn nnnnnnnnnn nnnnnnnnnn nnnnnnnngt catttccagg       120
aaatcaccgt catttccagg aaatcaccgt catttccagg aaatcaccnn nnnnnnnnnn       180
nnnnnnnnnn nnnnnnnnnn nnnnnnnnnn nnnnnngtca tttccaggaa atcaccgtca       240
tttccaggaa atcaccgtca tttccaggaa atcacc                                 276

<210> SEQ ID NO 8
<211> LENGTH: 384
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(108)
<223> OTHER INFORMATION: This region may encompass 0 to 48 variable
      nucleotide bases; a, c, g, or t
<220> FEATURE:
<221> NAME/KEY: modified_base
<222> LOCATION: (169)..(216)
<223> OTHER INFORMATION: This region may encompass 0 to 48 variable
      nucleotide bases; a, c, g, or t
<220> FEATURE:
<221> NAME/KEY: modified_base
<222> LOCATION: (277)..(324)
<223> OTHER INFORMATION: This region may encompass 0 to 48 variable
      nucleotide bases; a, c, g, or t

<400> SEQUENCE: 8
gtcatttcca ggaaatcacc gtcatttcca ggaaatcacc gtcatttcca ggaaatcacc        60
nnnnnnnnnn nnnnnnnnnn nnnnnnnnnn nnnnnnnnnn nnnnnnnngt catttccagg       120
aaatcaccgt catttccagg aaatcaccgt catttccagg aaatcaccnn nnnnnnnnnn       180
nnnnnnnnnn nnnnnnnnnn nnnnnnnnnn nnnnnngtca tttccaggaa atcaccgtca       240
tttccaggaa atcaccgtca tttccaggaa atcaccnnnn nnnnnnnnnn nnnnnnnnnn       300
nnnnnnnnnn nnnnnnnnnn nnnngtcatt tccaggaaat caccgtcatt tccaggaaat       360
caccgtcatt tccaggaaat cacc                                              384

<210> SEQ ID NO 9
<211> LENGTH: 240
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 9
gtcatttcca ggaaatcacc gtcatttcca ggaaatcacc gtcatttcca ggaaatcacc        60
gtcatttcca ggaaatcacc gtcatttcca ggaaatcacc gtcatttcca ggaaatcacc       120
gtcatttcca ggaaatcacc gtcatttcca ggaaatcacc gtcatttcca ggaaatcacc       180
gtcatttcca ggaaatcacc gtcatttcca ggaaatcacc gtcatttcca ggaaatcacc       240

<210> SEQ ID NO 10
<211> LENGTH: 264
<212> TYPE: DNA
<213> ORGANISM: Artificial Sequence

```
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(68)
<223> OTHER INFORMATION: This region may encompass 0 to 8 variable
      nucleotide bases; a, c, g, or t
<220> FEATURE:
<221> NAME/KEY: modified_base
<222> LOCATION: (129)..(136)
<223> OTHER INFORMATION: This region may encompass 0 to 8 variable
      nucleotide bases; a, c, g, or t
<220> FEATURE:
<221> NAME/KEY: modified_base
<222> LOCATION: (197)..(204)
<223> OTHER INFORMATION: This region may encompass 0 to 8 variable
      nucleotide bases; a, c, g, or t

<400> SEQUENCE: 10
gtcatttcca ggaaatcacc gtcatttcca ggaaatcacc gtcatttcca ggaaatcacc      60
nnnnnnnngt catttccagg aaatcaccgt catttccagg aaatcaccgt catttccagg     120
aaatcaccnn nnnnnngtca tttccaggaa atcaccgtca tttccaggaa atcaccgtca     180
tttccaggaa atcaccnnnn nnnngtcatt tccaggaaat caccgtcatt tccaggaaat     240
caccgtcatt tccaggaaat cacc                                            264

<210> SEQ ID NO 11
<211> LENGTH: 264
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 11
gtcatttcca ggaaatcacc gtcatttcca ggaaatcacc gtcatttcca ggaaatcacc      60
gccgtaccgt catttccagg aaatcaccgt catttccagg aaatcaccgt catttccagg     120
aaatcaccgc cgtaccgtca tttccaggaa atcaccgtca tttccaggaa atcaccgtca     180
tttccaggaa atcaccgccg taccgtcatt tccaggaaat caccgtcatt tccaggaaat     240
caccgtcatt tccaggaaat cacc                                            264

<210> SEQ ID NO 12
<211> LENGTH: 274
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(68)
<223> OTHER INFORMATION: This region may encompass 0 to 8 variable
      nucleotide bases; a, c, g, or t
<220> FEATURE:
<221> NAME/KEY: modified_base
<222> LOCATION: (129)..(138)
<223> OTHER INFORMATION: This region may encompass 0 to 10 variable
      nucleotide bases; a, c, g, or t
<220> FEATURE:
<221> NAME/KEY: modified_base
<222> LOCATION: (199)..(214)
<223> OTHER INFORMATION: This region may encompass 0 to 16 variable
      nucleotide bases; a, c, g, or t

<400> SEQUENCE: 12
gtcatttcca ggaaatcacc gtcatttcca ggaaatcacc gtcatttcca ggaaatcacc      60
```

```
nnnnnnnngt catttccagg aaatcaccgt catttccagg aaatcaccgt catttccagg      120
aaatcaccnn nnnnnnnngt catttccagg aaatcaccgt catttccagg aaatcaccgt      180
catttccagg aaatcaccnn nnnnnnnnnn nnnngtcatt tccaggaaat caccgtcatt      240
tccaggaaat caccgtcatt tccaggaaat cacc                                  274

<210> SEQ ID NO 13
<211> LENGTH: 274
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 13
gtcatttcca ggaaatcacc gtcatttcca ggaaatcacc gtcatttcca ggaaatcacc       60
gccgtaccgt catttccagg aaatcaccgt catttccagg aaatcaccgt catttccagg      120
aaatcaccta ccggtctggt catttccagg aaatcaccgt catttccagg aaatcaccgt      180
catttccagg aaatcaccac cggcctagtg cgtcgtcatt tccaggaaat caccgtcatt      240
tccaggaaat caccgtcatt tccaggaaat cacc                                  274

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taccggtctg                                                              10

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
accggcctag tgcgtc                                                       16

<210> SEQ ID NO 16
<211> LENGTH: 180
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 16
gtcatttcca ggaaatcacc gtcatttcca ggaaatcacc gtcatttcca ggaaatcacc       60
gtcatttcca ggaaatcacc gtcatttcca ggaaatcacc gtcatttcca ggaaatcacc      120
gtcatttcca ggaaatcacc gtcatttcca ggaaatcacc gtcatttcca ggaaatcacc      180

<210> SEQ ID NO 17
<211> LENGTH: 196
<212> TYPE: DNA
<213> ORGANISM: Artificial Sequence
<220> FEATURE:
```

<223> OTHER INFORMATION: Description of Artificial Sequence: Synthetic
      nucleotide construct
<220> FEATURE:
<221> NAME/KEY: modified_base
<222> LOCATION: (61)..(68)
<223> OTHER INFORMATION: This region may encompass 0 to 8 variable
      nucleotide bases; a, c, g, or t
<220> FEATURE:
<221> NAME/KEY: modified_base
<222> LOCATION: (129)..(136)
<223> OTHER INFORMATION: This region may encompass 0 to 8 variable
      nucleotide bases; a, c, g, or t

<400> SEQUENCE: 17
gtcatttcca ggaaatcacc gtcatttcca ggaaatcacc gtcatttcca ggaaatcacc    60
nnnnnnnngt catttccagg aaatcaccgt catttccagg aaatcaccgt catttccagg   120
aaatcaccnn nnnnnngtca tttccaggaa atcaccgtca tttccaggaa atcaccgtca   180
tttccaggaa atcacc                                                   196

<210> SEQ ID NO 18
<211> LENGTH: 196
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 18
gtcatttcca ggaaatcacc gtcatttcca ggaaatcacc gtcatttcca ggaaatcacc    60
gccgtaccgt catttccagg aaatcaccgt catttccagg aaatcaccgt catttccagg   120
aaatcaccgc cgtaccgtca tttccaggaa atcaccgtca tttccaggaa atcaccgtca   180
tttccaggaa atcacc                                                   196

<210> SEQ ID NO 19
<211> LENGTH: 198
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (61)..(68)
<223> OTHER INFORMATION: This region may encompass 0 to 8 variable
      nucleotide bases; a, c, g, or t
<220> FEATURE:
<221> NAME/KEY: modified_base
<222> LOCATION: (129)..(138)
<223> OTHER INFORMATION: This region may encompass 0 to 10 variable
      nucleotide bases; a, c, g, or t

<400> SEQUENCE: 19
gtcatttcca ggaaatcacc gtcatttcca ggaaatcacc gtcatttcca ggaaatcacc    60
nnnnnnnngt catttccagg aaatcaccgt catttccagg aaatcaccgt catttccagg   120
aaatcaccnn nnnnnnnngt catttccagg aaatcaccgt catttccagg aaatcaccgt   180
catttccagg aaatcacc                                                 198

<210> SEQ ID NO 20
<211> LENGTH: 198
<212> TYPE: DNA
<213> ORGANISM: Artificial Sequence
<220> FEATURE:
<223> OTHER INFORMATION: Description of Artificial Sequence: Synthetic
      nucleotide construct

```
<400> SEQUENCE: 20
gtcatttcca ggaaatcacc gtcatttcca ggaaatcacc gtcatttcca ggaaatcacc        60
gccgtaccgt catttccagg aaatcaccgt catttccagg aaatcaccgt catttccagg       120
aaatcaccta ccggtctggt catttccagg aaatcaccgt catttccagg aaatcaccgt       180
catttccagg aaatcacc                                                    198

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(5)
<223> OTHER INFORMATION: a, c, g, or t
<220> FEATURE:
<221> NAME/KEY: modified_base
<222> LOCATION: (15)..(20)
<223> OTHER INFORMATION: a, c, g, or t

<400> SEQUENCE: 21
nnnnnttcch ggaannnnnn                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(20)
<223> OTHER INFORMATION: a, c, g, or t

<400> SEQUENCE: 22
nnnntttcch ggaaannnnn                                                   20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(20)
<223> OTHER INFORMATION: a, c, g, or t

<400> SEQUENCE: 23
nnnntttccc cgaaannnnn                                                   20

<210> SEQ ID NO 24
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(20)
<223> OTHER INFORMATION: a, c, g, or t

<400> SEQUENCE: 24
nnnnattctc agaaannnnn                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(20)
<223> OTHER INFORMATION: a, c, g, or t

<400> SEQUENCE: 25
nnnntttcta ggaatnnnnn                                                    20

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(5)
<223> OTHER INFORMATION: a, c, g, or t
<220> FEATURE:
<221> NAME/KEY: modified_base
<222> LOCATION: (15)..(25)
<223> OTHER INFORMATION: a, c, g, or t
<220> FEATURE:
<221> NAME/KEY: modified_base
<222> LOCATION: (35)..(45)
<223> OTHER INFORMATION: a, c, g, or t
<220> FEATURE:
<221> NAME/KEY: modified_base
<222> LOCATION: (55)..(60)
<223> OTHER INFORMATION: a, c, g, or t

<400> SEQUENCE: 26
nnnnnttcch ggaannnnnn nnnnnttcch ggaannnnnn nnnnnttcch ggaannnnnn         60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
```

```
<221> NAME/KEY: modified_base
<222> LOCATION: (16)..(24)
<223> OTHER INFORMATION: a, c, g, or t
<220> FEATURE:
<221> NAME/KEY: modified_base
<222> LOCATION: (36)..(44)
<223> OTHER INFORMATION: a, c, g, or t
<220> FEATURE:
<221> NAME/KEY: modified_base
<222> LOCATION: (56)..(60)
<223> OTHER INFORMATION: a, c, g, or t

<400> SEQUENCE: 27
nnnntttcch ggaaannnnn nnnntttcch ggaaannnnn nnnntttcch ggaaannnnn    60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(24)
<223> OTHER INFORMATION: a, c, g, or t
<220> FEATURE:
<221> NAME/KEY: modified_base
<222> LOCATION: (36)..(44)
<223> OTHER INFORMATION: a, c, g, or t
<220> FEATURE:
<221> NAME/KEY: modified_base
<222> LOCATION: (56)..(60)
<223> OTHER INFORMATION: a, c, g, or t

<400> SEQUENCE: 28
nnnntttccc cgaaannnnn nnnntttccc cgaaannnnn nnnntttccc cgaaannnnn    60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(24)
<223> OTHER INFORMATION: a, c, g, or t
<220> FEATURE:
<221> NAME/KEY: modified_base
<222> LOCATION: (36)..(44)
<223> OTHER INFORMATION: a, c, g, or t
<220> FEATURE:
<221> NAME/KEY: modified_base
<222> LOCATION: (56)..(60)
<223> OTHER INFORMATION: a, c, g, or t

<400> SEQUENCE: 29
nnnnattctc agaaannnnn nnnnattctc agaaannnnn nnnnattctc agaaannnnn    60

<210> SEQ ID NO 30
<211> LENGTH: 60
<212> TYPE: DNA
<213> ORGANISM: Artificial Sequence
```

```
<220> FEATURE:
<223> OTHER INFORMATION: Description of Artificial Sequence: Synthetic
      nucleotide construct
<220> FEATURE:
<221> NAME/KEY: modified_base
<222> LOCATION: (1)..(4)
<223> OTHER INFORMATION: a, c, g, or t
<220> FEATURE:
<221> NAME/KEY: modified_base
<222> LOCATION: (16)..(24)
<223> OTHER INFORMATION: a, c, g, or t
<220> FEATURE:
<221> NAME/KEY: modified_base
<222> LOCATION: (36)..(44)
<223> OTHER INFORMATION: a, c, g, or t
<220> FEATURE:
<221> NAME/KEY: modified_base
<222> LOCATION: (56)..(60)
<223> OTHER INFORMATION: a, c, g, or t

<400> SEQUENCE: 30
nnnntttcta ggaatnnnnn nnnntttcta ggaatnnnnn nnnntttcta ggaatnnnnn    60

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgtcatttcc aggaaatcac cgtcatttcc aggaaatcac cgtcatttcc aggaaatcac    60
cgc                                                                 63

<210> SEQ ID NO 32
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtgatttcc tggaaatgac ggtgatttcc tggaaatgac ggtgatttcc tggccctgac    60
ggtac                                                               65

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggtcccaggt ccacttcgca tattaaggtg acgcgtgtgg cctcgaacac ca           52

<210> SEQ ID NO 34
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
agcttggtgt tcgaggccac acgcgtcacc ttaatatgcg aagtggacct gggaccgc     58
```

<210> SEQ ID NO 35
<211> LENGTH: 123
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 35

```
gtaccgtcat ttccaggaaa tcaccgtcat ttccaggaaa tcaccgtcat ttccaggaaa     60
tcaccgcggt cccaggtcca cttcgcatat taaggtgacg cgtgtggcct cgaacaccaa    120
gct                                                                  123
```

<210> SEQ ID NO 36
<211> LENGTH: 101
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 36

```
tctagactcg acatgctggg gccctgcatg ctgctgctgc tgctgctgct gggcctgagg     60
ctacagctct ccctgggcat catcgcggcc gcaggcatca t                        101
```

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
gcgcacccgg gggctagcta aggtacc                                         27
```

<210> SEQ ID NO 38
<211> LENGTH: 131
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 38

```
gtaccgtcat ttccaggaaa tcaccgtcat ttccaggaaa tcaccgtcat ttccaggaaa     60
tcaccgccgt acggcggtcc caggtccact tcgcatatta aggtgacgcg tgtggcctcg    120
aacaccaagc t                                                         131
```

<210> SEQ ID NO 39
<211> LENGTH: 324
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 39

```
gcaagtgcag gtgccagaac atttctctat cgataggtac cgtcatttcc aggaaatcac     60
cgtcatttcc aggaaatcac cgtcatttcc aggaaatcac cgccgtaccg tcatttccag    120
gaaatcaccg tcatttccag gaaatcaccg tcatttccag gaaatcaccg ccgtaccgtc    180
```

-continued

```
atttccagga aatcaccgtc atttccagga aatcaccgtc atttccagga aatcaccgcg    240
gtcccaggtc cacttcgcat attaaggtga cgcgtgtggc ctcgaacacc aagctctaga    300
ctcgacatgc tggggccctg catg                                           324

<210> SEQ ID NO 40
<211> LENGTH: 255
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 40
cgtcatttcc aggaaatcac cgtcatttcc aggaaatcac cgtcatttcc aggaaatcac     60
cgccgtaccg tcatttccag gaaatcaccg tcatttccag gaaatcaccg tcatttccag    120
gaaatcaccg ccgtaccgtc atttccagga atcaccgtc atttccagga atcaccgtc    180 atttccagga aatcaccgcg gtcccaggtc cacttcgcat attaaggtga cgcgtgtggc    240
ctcgaacacc aagct                                                     255

<210> SEQ ID NO 41
<211> LENGTH: 199
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 41
cgtcatttcc aggaaatcac cgtcatttcc aggaaatcac cgtcatttcc aggaaatcac     60
cgccgtaccg tcatttccag gaaatcaccg tcatttccag gaaatcaccg tcatttccag    120
gaaatcaccg ccgtaccgtc atttccagga atcaccgtc atttccagga atcaccgtc    180 atttccagga aatcaccgc                                                 199
```

RESPONSE ELEMENT REGIONS

This application claims the benefit of U.S. Provisional Application No. 60/564,724, filed Apr. 22, 2004; and U.S. Provisional Application No. 60/565,135, filed Apr. 23, 2004. U.S. Provisional Application Nos. 60/564,724 and 60/565,135 are incorporated by reference herein for any purpose.

FIELD

Response element regions, DNA constructs comprising response element regions, host cells comprising response element regions, and methods of using response element regions are provided.

BACKGROUND

In certain cellular systems, certain molecules, such as cytokines and growth factors, can interact with a receptor of a cell, which triggers a process that affects the activity of one or more transcription factor. In certain instances, the process activates one or more transcription factors, which then bind to a response element region of a gene to induce transcription. In certain instances, the transcription factor is a Signal Transducer and Activator of Transcription (STAT).

SUMMARY OF THE INVENTION

In certain embodiments, an isolated nucleic acid comprising a response element region is provided. In certain embodiments, a vector comprising a promoter and nucleic acid comprising a response element region is provided. In certain embodiments, a host cell comprising a vector is provided.

In certain embodiments, a response element region comprises (i) the sequence GTCATTTCCAGGAAATCACC (SEQ ID NO: 1) or (ii) a sequence complementary to the sequence in (i).

In certain embodiments, a response element region comprises (i) the sequence GTCATTTCCAGGAAATCACCGTCATTTCCAGGAAATCACCGTCATT TCCAGGAAAT-CACC (SEQ ID NO: 2) or (ii) a sequence complementary to the sequence in (i). In certain embodiments, a response element region comprises (i) the sequence GTCATTTCCAGGAAATCACCGTCATTTCCAGGAAATCAC-CGTCATTTCC AGGAAATCACC-Y-GTCATTTCCAGGAAATCACCGTCATTTCCAGGAAAT-CACCGTC ATTTCCAGGAAATCACC (SEQ ID. NO: 3) or (ii) a sequence complementary to the sequence in (i). In certain embodiments, a response element region comprises (i) the sequence GTCATTTCCAGGAAATCACCGT-CATTTCCAGGAAATCACCGTCATTTC CAGGAAAT-CACC-Y-GTCATTTCCAGGAAATCACCGTCATTTC-CAGGAAATCAC CGTCATTTCCAGGAAATCACC-X-GTCATTTCCAGGAAATCACCGTCATT TCCAGGAAATCACCGTCATT TCCAGGAAATCACC (SEQ ID NO: 4) or (ii) a sequence complementary to the sequence in (i). In certain embodiments, a response element region comprises (i) the sequence GTCATTTCCAGGAAAT-CACCGTCATT TCCAGGAAATCACCGTCATTTCCAG-GAAATCACC-Y-GTCATTTCCAGGAAA TCACCGT-CATTTCCAGGAAATCACCGTCATTTCCAGGAAATCA-CC-X-GTCATTTCCAGGAAATCACCGTCATTTC-CAGGAAATCACCGTCATTTCCAGGAAAT CACC-Z-GTCATTCCAGGAAATCACCGTCATTTC-CAGGAAATCACCGTCA TTTCCAGGAAATCACC (SEQ ID NO: 5) or (ii) a sequence complementary to the sequence in (i). In certain embodiments, Y, X, and Z are each independently selected from a nucleic acid sequence of 0 to 23 nucleotides.

In certain embodiments, a method for determining the activity of a test composition comprising a signaling molecule is provided. In certain embodiments, the method comprises contacting the test composition with a signaling molecule-responsive host cell comprising a vector that comprises a promoter and nucleic acid comprising a response element region. In certain embodiments, the method further comprises incubating the test composition comprising a signaling molecule and the signaling-responsive host cell under conditions in which the reporter nucleic acid expresses a reporter protein in response to the signaling molecule. In certain embodiments, the method further comprises detecting the reporter protein to determine the activity of the test composition.

In certain embodiments, a method for determining whether a test compound has activity of a given signaling molecule is provided. In certain embodiments, the method comprises contacting the test compound with a signaling molecule-responsive host cell comprising a vector that comprises a promoter and nucleic acid comprising a response element region. In certain embodiments, the method further comprises incubating the test compound and the signaling-responsive host cell under conditions in which the reporter nucleic acid expresses a reporter protein in response to the signaling molecule. In certain embodiments, the method further comprises detecting the reporter protein to determine the activity of the test composition. In certain embodiments, the method further comprises comparing the level of detected reporter protein expression with the level of detected reporter protein expressed by a signaling molecule-responsive host cell comprising the vector in the absence of the test compound to determine whether the test compound has the activity of the given signaling molecule. In certain embodiments, the method further comprises comparing the level of detected reporter protein expression with the level of detected reporter protein expressed by a signaling molecule-responsive host cell comprising the vector in the presence of the given signaling molecule, but in the absence of the test compound to determine whether the test compound has the activity of the given signaling molecule.

In certain embodiments, a method for determining whether a test compound impacts the activity of a signaling molecule is provided. In certain embodiments, the method comprises contacting the test compound with a signaling molecule-responsive host cell comprising a vector that comprises a promoter and nucleic acid comprising a response element region in the presence of the signaling molecule under conditions in which the reporter nucleic acid expresses a reporter protein in response to the signaling molecule. In certain embodiments, the method further comprises detecting the reporter protein. In certain embodiments, the method further comprises comparing the level of detected reporter protein expression with the level of detected reporter protein expressed by a signaling molecule-responsive host cell comprising the vector in the presence of the signaling molecule, but in the absence of the test compound, to determine whether the test compound impacts the activity of the signaling molecule.

In certain embodiments, a method of producing a polypeptide from an ex vivo mammalian system is provided. In certain embodiments, the method comprises producing the polypeptide. In certain embodiments, the method further comprises testing the polypeptide with a signaling molecule-responsive host cell comprising a vector that comprises a promoter and nucleic acid comprising a response element region. In certain embodiments, the method further comprises determining the amount of protein produced and/or activity of the protein produced by the ex vivo system.

In certain embodiments, a response element region comprising more than one response element sequences is provided. In certain embodiments, a response element sequence comprises the sequence GTCATTTCCAGGAAATCACC SEQ ID NO: 1). In certain embodiments, the center region of at least two response element sequences are spatially oriented to be in the same location (on the y and z axis) plus or minus 36 degrees, relative to the center axis of the double-helical DNA (x-axis). In certain embodiments, the center region is the tenth and eleventh nucleotides AG of the sequence GTCATTTCCAGGAAATCACC (SEQ ID NO: 1).

In certain embodiments, a response element region comprising more than one response element sequence core regions is provided. In certain embodiments, a response element sequence core region comprises the sequence TTCCAGGAA. In certain embodiments, the center region of at least two response element sequence core regions are spatially oriented to be in the same location (on the y and z axis) plus or minus 36 degrees, relative to the center axis of the double-helical DNA (x-axis). In certain embodiments, the center region is the fifth and sixth nucleotides AG of the sequence TTCCAGGAA. In certain embodiments, a response element region comprising at least two series of more than one response element sequences is provided. In certain embodiments, a response element sequence comprises the sequence GTCATTTCCAGGAAATCACC (SEQ ID NO: 1). In certain embodiments, each series of more than one response element sequences are linked together by a sequence of approximately eight nucleotides. In certain embodiments, within a first series of the response element sequences, each center region of the response element sequences are spatially oriented to be in approximately the same location (on the y and z axis) plus or minus 36 degrees, relative to the center axis of the double-helical DNA (x-axis). In certain embodiments, the center region is the tenth and eleventh nucleotides AG of the sequence GTCATTTCCAGGAAATCACC (SEQ ID NO: 1). In certain embodiments, within a second series of the response element sequences, each center region of the response element sequences are spatially oriented to be in approximately the same location (on the y and z axis) plus or minus 36 degrees, relative to the center axis of the double-helical DNA (x-axis). In certain embodiments, the center region is the tenth and eleventh nucleotides AG of the sequence GTCATTTCCAGGAAATCACC (SEQ ID NO: 1). In certain embodiments, the center region of the response element sequences of the second series are spatially oriented to be approximately 72 to 86 degrees from the center region of the first series of the response element sequences as determined from the y and z axis relative to the center axis of the double-helical DNA as the x axis.

In certain embodiments, a response element region comprising at least two series of more than one response element sequences is provided. In certain embodiments, a response element sequence comprises the sequence GTCATTTCCAGGAAATCACC (SEQ ID NO: 1). In certain embodiments, each series of more than one response element sequences are linked together by a sequence of approximately eight nucleotides. In certain embodiments, within a first series of the response element sequences, each center region of the response element sequences are spatially oriented to be in approximately the same location (on the y and z axis) plus or minus 36 degrees, relative to the center axis of the double-helical DNA (x-axis). In certain embodiments, the center region is the tenth and eleventh nucleotides AG of the sequence GTCATTTCCAGGAAATCACC (SEQ ID NO: 1). In certain embodiments, within a second series of the response element sequences, each center region of the response element sequences are spatially oriented to be in approximately the same location (on the y and z axis) plus or minus 36 degrees, relative to the center axis of the double-helical DNA (x-axis). In certain embodiments, the center region is the tenth and eleventh nucleotides AG of the sequence GTCATTTCCAGGAAATCACC (SEQ ID NO: 1). In certain embodiments, the center region of the response element sequences of the second series of the response element sequences are spatially oriented to be approximately 144 to 180 degrees (in certain embodiments, from 144 to 172 degrees) from the center region of the first series of the response element sequences as determined from the y and z axis relative to the center axis of the double-helical DNA as the x axis.

BRIEF DESCRIPTION OF THE FIGURES

FIG. 1 also depicts the x, y, and z axis.

DETAILED DESCRIPTION OF CERTAIN PREFERRED EMBODIMENTS

Figure 1:
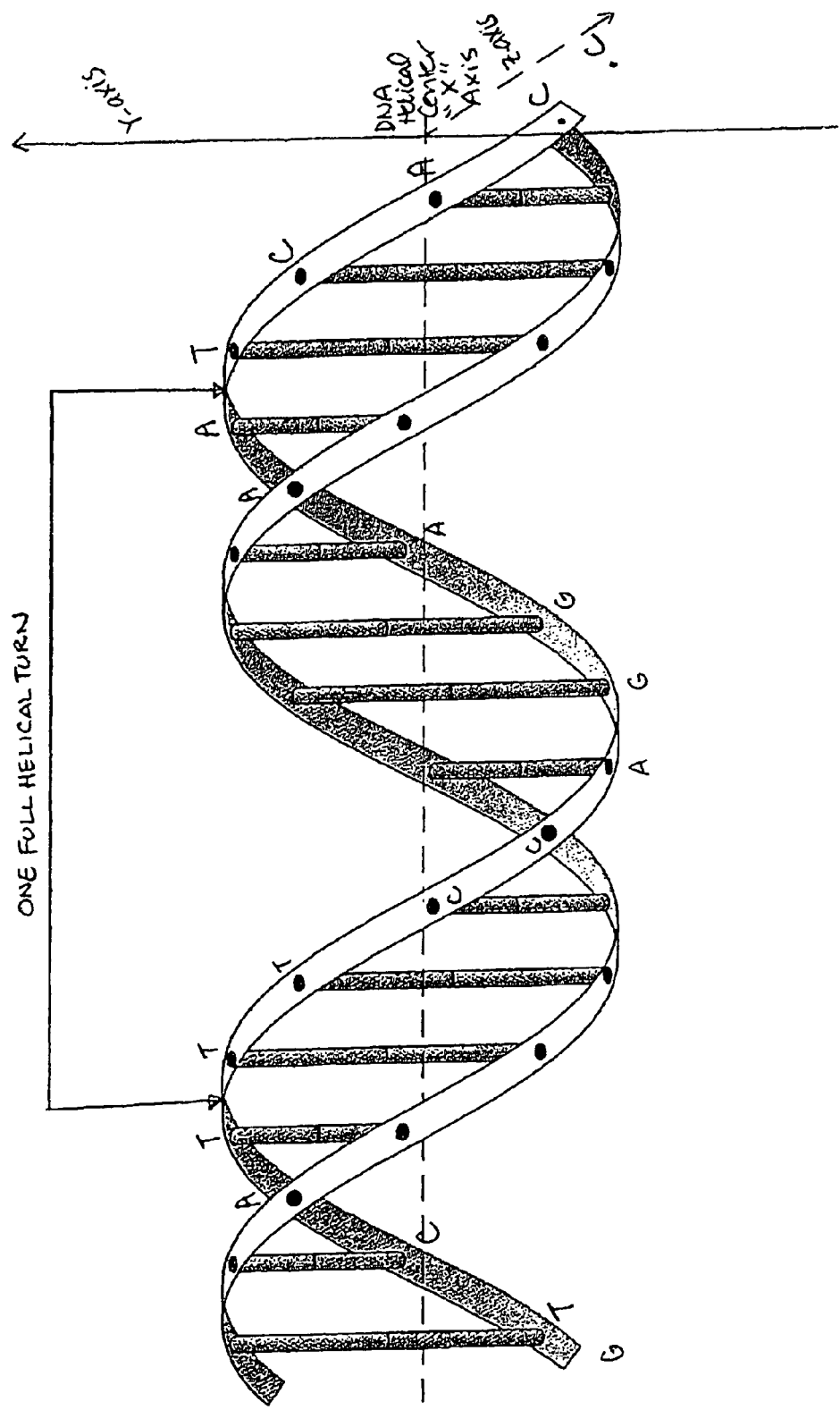
FIG. 1 is an exemplary representation of the sequence GTCATTTCCAGGAAATCACC (SEQ ID NO: 1) on a double helix DNA.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

Standard techniques may be used for recombinant DNA, oligonucleotide synthesis, and tissue culture and transfection (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

A response element region refers to a region of a double-stranded nucleic acid that is capable of being bound by one or more activated response element transcription factors, or one or more complexes of activated response element transcription factors, to modulate expression of one or more genes. A response element region also refers to a region of a single-stranded nucleic acid that, if it were double-stranded DNA, would be capable of being bound by one or more activated response element transcription factors, or one or more complexes of activated response element transcription factors, to modulate expression of one or more genes.

The term response element transcription factors refers to factors that bind to a response element region to modulate expression of one or more genes. In certain embodiments, multiple response element transcription factors may bind to a response element region. In certain embodiments, one or more complexes of response element transcription factors may bind to a response element region.

The term "operably linked" refers to components that are in a relationship permitting them to function in their intended manner. For example, a control sequence "operably linked" to a coding sequence permits expression of the coding sequence under conditions compatible with the operation of the control sequence.

The term "control sequence" refers to a nucleic acid sequence which may effect the expression and processing of coding sequences. According to certain embodiments, control sequences may include response element regions and promoters.

A signaling molecule refers to an extracellular molecule, in either a free or bound form, that interacts with a receptor of a cell, which triggers a process that affects the activity of one or more response element transcription factors.

A signaling molecule-responsive host cell refers to a host cell that comprises a signaling molecule receptor capable of interacting with a signaling molecule.

The term "reporter nucleic acid" refers to a nucleic acid that encodes a polypeptide that can be used to detect expression of the reporter nucleic acid.

The term "isolated nucleic acid" or "isolated polynucleotide" as used herein shall mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is linked to a nucleic acid which it is not linked to in nature, or (3) does not occur in nature as part of a larger sequence.

The term "nucleic acid" or "polynucleotide" as referred to herein means a polymeric form of nucleotides. In certain embodiments, the bases may comprise at least one of ribonucleotides, deoxyribonucleotides, and a modified form of either type of nucleotide. The term includes single and double stranded forms of DNA.

The term "naturally occurring nucleotides" includes deoxyribonucleotides and ribonucleotides. Deoxyribonucleotides include, but are not limited to, adenosine, guanine, cytosine, and thymidine. Ribonucleotides include, but are not limited to, adenosine, cytosine, thymidine, and uricil. The term "modified nucleotides" includes nucleotides with modified or substituted sugar groups and the like. The term "oligonucleotide linkages" includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990). In certain instances, an oligonucleotide can include a label for detection.

The term "polypeptide" is used herein as a generic term to refer to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than those normally encoded by a codon.

Polypeptides include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. Such modifications may be present to the same or varying degrees at several sites in a given polypeptide. Also, in certain embodiments, a given polypeptide may contain many types of modifications such as deletions, additions, and/or substitutions of one or more amino acids of a native sequence. In certain embodiments, polypeptides may be branched as a result of ubiquitination, and, in certain embodiments, they may be cyclic, with or without branching. Cyclic, branched and branched cyclic polypeptides may result from post-translation natural processes or may be made by synthetic methods. Modifications include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAM J. Applied Math.*, 48:1073 (1988). A protein is "substantially similar" to another protein, as it is meant herein, when it is at least 90% identical to the other protein in amino acid sequence and maintains or alters in a desirable manner the biological activity of the unaltered polypeptide. Biological activity can be measured by an in vivo assay such as that described by Cotes and Bangham ((1961), Nature 191: 1065-67).

Certain methods to determine identity are designed to give the largest match between the sequences tested. Certain, methods to determine identity are described in publicly available computer programs. Certain computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see Dayhoff et al., *Atlas of Protein Sequence and Structure*, 5(3)(1978) for the PAM 250 comparison matrix; Henikoff et al., *Proc. Natl. Acad. Sci* USA, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters.

In certain embodiments, the aforementioned parameters are the default parameters for polypeptide comparisons (along with no penalty for end gaps) using the GAP algorithm.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include, but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded nucleic acid sequences is the 5' end; the left-hand direction of double-stranded nucleic acid sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | More specific exemplary Substitutions |
| --- | --- | --- |
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity, including but not limited to the CDRs of an antibody, or that may be important for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a polypeptide that correspond to amino acid residues which are important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three dimensional structure. In certain embodiments, one skilled in the art may choose not to make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3): 377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, polypeptide variants comprise a greater or a lesser number of N-linked glycosylation sites than the native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

In certain embodiments, polypeptide variants include cysteine variants. In certain embodiments, cysteine variants have one or more cysteine residues that are deleted from or that are replaced by another amino acid (e.g., serine) as compared to the parent amino acid sequence. In certain embodiments, cysteine variants have one or more cysteine residues that are added to or that replace another amino acid (e.g., serine) as compared to the parent amino acid sequence. In certain embodiments, cysteine variants may be useful when polypeptides are refolded into a biologically active conformation such as after the isolation of insoluble inclusion bodies. In certain embodiments, cysteine variants have fewer cysteine residues than the native polypeptide. In certain embodiments, cysteine variants have more cysteine residues than the native polypeptide. In certain embodiments, cysteine variants have an even number of cysteine residues to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino-terminal and/or carboxy-terminal deletion. In certain embodiments, fragments are at least 5 to 467 amino acids long. It will be appreciated that in certain embodiments, fragments are at least 5, 6, 8, 10, 14, 20, 50, 70, 100, 150, 200, 250, 300, 350, 400, or 450 amino acids long.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger TINS p. 392 (1985); and Evans et al. *J. Med. Chem.* 30:1229 (1987). Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —$CH$=$CH$— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992)); for example, by adding internal cysteine residues capable of forming intramolecular disulfide bridges which cyclize the peptide.

"Antibody" or "antibody peptide(s)" both refer to an intact antibody, or a fragment thereof. In certain embodiments, the antibody fragment may be a binding fragment that competes with the intact antibody for specific binding. The term "antibody" also encompasses polyclonal antibodies and monoclonal antibodies. In certain embodiments, binding fragments are produced by recombinant DNA techniques. In certain embodiments, binding fragments are produced by enzymatic or chemical cleavage of intact antibodies. In certain embodiments, binding fragments are produced by recombinant DNA techniques. Binding fragments include, but are not limited to, Fab, Fab', F(ab')$_2$, Fv, Facb, and single-chain antibodies. Non-antigen binding fragments include, but are not limited to, Fc fragments.

"Chimeric antibody" refers to an antibody that has an antibody variable region of a first species fused to another molecule, for example, an antibody constant region of another second species. In certain embodiments, the first species may be different from the second species. In certain embodiments, the first species may be the same as the second species. In certain embodiments, chimeric antibodies may be made through mutagenesis or CDR grafting to match a portion of the known sequence of an antibody variable region. CDR grafting typically involves grafting the CDRs from an antibody with desired specificity onto the framework regions (FRs) of another antibody.

A bivalent antibody other than a "multispecific" or "multifunctional" antibody, in certain embodiments, typically is understood to have each of its binding sites identical.

An antibody substantially inhibits adhesion of a ligand to a receptor when an excess of antibody reduces the quantity of receptor bound to the ligand by at least about 20%, 40%, 60%, 80%, 85%, or more (as measured in an in vitro competitive binding assay).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. An antibody specifically binds an antigen when it preferentially recognizes its target antigen in a complex mixture of proteins and/or macromolecules. In certain embodiments, an antibody specifically binds an antigen when the dissociation constant is $\leq 1$ μM, in certain embodiments, when the dissociation constant is $\leq 100$ nM, and in certain embodiments, when the dissociation constant is $\leq 10$ nM.

As used herein, the term "label" refers to any molecule that can be detected. In a certain embodiment, a polypeptide may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the polypeptide. In certain embodiments, a label may be incorporated into or attached to another reagent which in turn binds to the antibody of interest. For example, a label may be incorporated into or attached to a polypeptide that in turn specifically binds the polypeptide of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Examples of labels for polypeptides include, but are not limited to, the following: radioisotopes or radionucleoides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., fluorescein isothiocyanate (FITC), rhodamine lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehydrogenase, penicillinase), chemiluminescent, biotinyl groups, predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "sample", as used herein, includes, but is not limited to, any quantity of a substance. In certain embodiments, a sample may be from a chemical reaction, including, but not limited to, a protein synthesis reaction.

The term "pharmaceutical agent or drug" as used herein refers to a chemical compound or composition capable of inducing a desired therapeutic effect when properly administered to a patient.

The term "modulator," as used herein, is a compound that changes or alters the activity or function of a molecule. For example, a modulator may cause an increase or decrease in the magnitude of a certain activity or function of a molecule compared to the magnitude of the activity or function of the molecule in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates or small organic molecules. Peptibodies are described, e.g., in WO 01/83525.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term "patient" includes human and animal subjects.

Certain Exemplary Response Element Regions and Reporter Nucleic Acid Constructs

As discussed above, a response element region refers to a region of a double-stranded nucleic acid that is capable of being bound by one or more activated response element transcription factors, or one or more complexes of activated response element transcription factors, to modulate expression of one or more genes. A response element region also refers to a region of a single-stranded nucleic acid that, if it were double-stranded DNA, would be capable of being bound by one or more activated response element transcription factors, or one or more complexes of activated response element transcription factors, to modulate expression of one or more genes. In this patent application, discussion of one or more transcription factor binding to a response element region encompasses binding by one or more transcription factor and/or binding by one or more complexes of activated transcription factors. In certain embodiments, a response element region is provided.

In certain embodiments, a response element region is included in a reporter nucleic acid construct, which is transfected into a signaling molecule-responsive host cell. In certain embodiments, a reporter nucleic acid construct comprises at least a response element region, a promoter, and a reporter nucleic acid in operable combination. In certain embodiments, when a signaling molecule interacts with a signaling molecule receptor of the host cell, a process is triggered that results in activation of one or more response element transcription factor. In certain embodiments, the activated one or more response element transcription factor binds to the response element region of the reporter nucleic acid construct, which results in expression of the reporter nucleic acid. In certain embodiments, one can then detect the production of the reporter polypeptide to determine the activity of the signaling molecule.

Certain embodiments involve response element transcription factors that are known as Signal Transducers and Activators of Transcription (STAT). At least seven members of the STAT family of proteins have been identified in mammals, including Stat1, Stat2, Stat3, Stat4, Stat5a, Stat5b, and Stat6. The term STAT5 encompasses both STAT5a or STAT5. Cytokine or growth factor binding to certain cell surface receptors results in tyrosine phosphorylation and activation of STATs in the cytoplasm. Phosphorylated STATs form dimers through reciprocal phosphotyrosine-SH2 interactions. The activated STAT dimers translocate to the nucleus, where they activate transcription of STAT-responsive genes by binding to STAT-specific DNA response elements. See, e.g., Turkson et al. (2000) *Oncogene,* 19: 6613 and references cited therein.

STAT proteins serve a diverse array of biological functions, including, but not limited to, roles in differentiation, proliferation, development, apoptosis, and inflammation. The important physiological role of certain STATs has been demonstrated through various mouse knock-out experiments. For example, Stat2 null mice and Stat3 null mice are both embryonic lethal, while Stat1 null mice show high susceptibility to certain infections, reduced interferon responses, and higher incidence of certain tumors. Stat5a and/or Stat5b knockout mice are viable but show a variety of tissue-specific defects. See, e.g., Turkson et al. (2000) *Oncogene,* 19: 6613 and references cited therein.

In certain embodiments, a response element region that can be bound by STAT5 is provided. In certain embodiments, a response element region comprises (i) the sequence GTCATTTCCAGGAAATCACC (SEQ ID NO: 1) or (ii) a sequence complementary to the sequence in (i).

In certain embodiments, the response element region comprises:

(a) (i) the sequence GTCATTTCCAGGAAATCACCGT-CATTTCCAGGAAATCACCGTCATTTC-CAGGAAAT CACC (SEQ ID NO: 2) or (ii) a sequence complementary to the sequence in (i);

(b) (i) the sequence GTCATTTCCAGGAAATCACCGT-CATTTCCAGGAAATCACCGTCATTTC-CAGGAAAT CACC-Y-GTCATTTCCAGGAAAT-CACCGTCATTTCCAGGAAATCACCG TCATTTCCAGGAAATCACC (SEQ ID NO: 6) or (ii) a sequence complementary to the sequence in (i);

(c) (i) the sequence GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGT CATTTCCAGGAAATCACC-X-GTCATTTCCAGGAAATCACCGTCATTTCCAGG AAATCACCGTCATTTCCAGGAAATCACC (SEQ ID NO: 7) or (ii) a sequence complementary to the sequence in (i); or (d) (i) the sequence GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGT CATTTCCAGGAAATCACC-X-GTCATTTCCAGGAAATCACCGTCATTTCCAGG AAATCACCGTCATTTCCAGGAAATCACC-Z-GT-CATTTCCAGGAAATCACCGT CATTTCCAGGAAAT-CACCGTCATTTCCAGGAAATCACC (SEQ ID NO: 8) or (ii) a sequence complementary to the sequence in (i);

wherein Y, X, and Z are each independently selected from a nucleic acid sequence of 0 to 48 (including any integer within that range) nucleotides. In certain embodiments, Y, X, and Z are each independently selected from a nucleic acid sequence of 0 to 23 nucleotides.

In certain embodiments, Y, X, and/or Z may serve as spacer elements to provide space between multiple triple repeat sequences. In certain embodiments, a spacer element is a multiple of 10 to 12 nucleotides long, which results in the center regions of the sequences GTCATTTCCAGGAAAT-CACC (SEQ ID NO: 1) being spatially oriented to be in approximately the same location (on the y and z axis) plus or minus 36 degrees, relative to the center axis of the double-helical DNA (x-axis), wherein the center region is the tenth and eleventh nucleotides AG of the sequence GTCATTTC-CAGGAAATCACC (SEQ ID NO: 1). FIG. 1 is an exemplary representation of the sequence GTCATTTCCAGGAAAT-CACC (SEQ ID NO: 1) on a double helix DNA. FIG. 1 also depicts the x, y, and z axis.

In certain embodiments, a spacer element is 10 to 12 nucleotides long. In certain embodiments, a spacer element is 20 to 24 nucleotides long. In certain embodiments, a spacer element is 23 nucleotides long. In certain embodiments, a spacer element is 30 to 36 nucleotides long. In certain embodiments, a spacer element is 8 to 12 nucleotides long. In certain embodiments, a spacer element is 16 to 24 nucleotides long. In certain embodiments, a spacer element is 24 to 36 nucleotides long.

In certain embodiments, Y, X, and/or Z may serve a functional role in transcription. For example, in certain embodiments, transcription factors may bind to Y, X, and/or Z. Exemplary transcription factors that may bind may bind to Y, X, and/or Z, include, but are not limited to, NFAT, AP-1, CRE, NFκB, and members of the STAT protein family.

In certain embodiments, an isolated nucleic acid comprises the sequence: GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGTCATTTC CAGGAAATCACC-X-GTCATTTCCAGGAAATCACCGTCATTTC-CAGGAAATCACCGT CATTTCCAGGAAATCACC-Z-GTCATTTCCAGGAAATCACCGTCATTTCCAGGAAAT-C ACCGTCATTTCCAGGAAATCACC, wherein Y, X, and Z are each a nucleic acid sequence of 0 nucleotides (SEQ ID NO: 9).

In certain embodiments, an isolated nucleic acid comprises the sequence: GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGTCATTTCC AGGAAATCACC-X-GTCATTTCCAGGAAATCACCGTCATTTC-CAGGAAATCACCG TCATTTCCAGGAAATCACC-Z-GTCATTTCCAGGAAATCACCGTCATTTCCAGG AAATCACCGTCATTTCCAGGAAATCACC, wherein Y, X, and Z are each a nucleic acid sequence of 8 nucleotides (SEQ ID NO: 10). In certain embodiments, Y, X, and Z are each the nucleic acid sequence GCCGTACC (construct is SEQ ID NO: 11).

In certain embodiments, an isolated nucleic acid comprises the sequence: GTCATTTCCAGGAAATCACCGT-CATTTCCAGGAAATCACCGTCATTTC-CAGGAAAT CACC-Y-GTCATTTCCAGGAAAT-CACCGTCATTTCCAGGAAATCACCGTCATTTCC-A GGAAATCACC-X-GTCATTTCCAGGAAATCAC-CGTCATTTCCAGGAAATCACCGTCA TTTCCAG-GAAATCACC-Z-GTCATTTCCAGGAAATCAC-CGTCATTTCCAGGAAATCAC CGTCATTTCCAGGAAATCACC, wherein Y is a nucleic acid sequence of 8 nucleotides, X is a nucleic acid sequence of 10 nucleotides, and Z is a nucleic acid sequence of 16 nucleotides (SEQ ID NO: 12). In certain embodiments, Y is the nucleic acid sequence GCCG-TACC, X is the nucleic acid sequence TACCGGTCTG (SEQ ID NO: 14), and Z is the nucleic acid sequence ACCGGCCTAGTGCGTC (SEQ ID NO: 15), (construct is SEQ ID NO: 13).

In certain embodiments, an isolated nucleic acid comprises the sequence: GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGTCATTTCC AGGAAATCACC-X-GTCATTTCCAGGAAATCACCGTCATTTC-CAGGAAATCACCGT CATTTCCAGGAAATCACC, wherein Y and X are each a nucleic acid sequence of 0 nucleotides (SEQ ID NO: 16).

In certain embodiments, an isolated nucleic acid comprises the sequence: GTCATTTCCAGGAAATCACCGT-CATTTCCAGGAAATCACCGTCATTTCCAGGAAAT CACC-Y-GTCATTTCCAGGAAATCACCGTCATTTC-CAGGAAATCACCGTCATTTCCA GGAAATCACC-X-GTCATTTCCAGGAAATCACCGTCATTTC-CAGGAAATCACCGTCA TTTCCAGGAAATCACC, wherein Y and X are each a nucleic acid sequence of 8 nucleotides (SEQ ID NO: 17). In certain embodiments, Y and X are each the nucleic acid sequence GCCGTACC (construct is SEQ ID NO: 18).

In certain embodiments, an isolated nucleic acid comprises the sequence: GTCATTTCCAGGAAATCACCGT-CATTTCCAGGAAATCACCGTCATTTCCAGGAAAT CACC-Y-GTCATTTCCAG GAAATCACCGTCATTTC-CAG GAAATCACCGTCATTTCCA GGAAATCACC-X-GTCATTTCCAGGAAATCACCGTCATTTC-CAGGAAATCACCGTC ATTTCCAGGAAATCACC, wherein Y is a nucleic acid sequence of 8 nucleotides and X is a nucleic acid sequence of 10 nucleotides (SEQ ID NO: 19). In certain embodiments, Y is the nucleic acid sequence GCCGTACC and X is the nucleic acid sequence TACCGGTCTG (SEQ ID NO: 14), (construct is SEQ ID NO: 20).

In certain embodiments, a response element region comprises:

(i) the sequence $N_5$TTCCQGGAAN$_6$ (SEQ ID NO: 21); wherein $N_5$ is a sequence of five nucleotides independently selected from A, T, C, or G; $N_6$ is a sequence of six nucleotides independently selected from A, T, C, or G; and Q is nucleotide A, C, or T; or (ii) a sequence complementary to the sequence in (i). In certain embodiments, Q is the nucleotide A. In certain embodiments, Q is the nucleotide C. In certain embodiments, Q is the nucleotide T.

In certain embodiments, a response element region comprises:

(i) the sequence $N_4$TTTCCQGGAAAN$_5$ (SEQ ID NO: 22); wherein $N_4$ is a sequence of four nucleotides independently selected from A, T, C, or G; $N_5$ is a sequence of five nucleotides independently selected from A, T, C, or G; and Q is nucleotide A, C, or T; or (ii) a sequence complementary to the sequence in (i). In certain embodiments, Q is the nucleotide A. In certain embodiments, Q is the nucleotide C. In certain embodiments, Q is the nucleotide T.

In certain embodiments, a response element region comprises:

(i) the sequence $N_4$TTTCCCCGAAAN$_5$ (SEQ ID NO: 23); wherein $N_4$ is a sequence of four nucleotides independently selected from A, T, C, or G and $N_5$ is a sequence of five nucleotides independently selected from A, T, C, or G; or (ii) a sequence complementary to the sequence in (i).

In certain embodiments, a response element region comprises:

(i) the sequence $N_4$ATTCTCAGAAAN$_5$ (SEQ ID NO: 24); wherein $N_4$ is a sequence of four nucleotides independently selected from A, T, C, or G and $N_5$ is a sequence of five nucleotides independently selected from A, T, C, or G; or (ii) a sequence complementary to the sequence in (i).

In certain embodiments, a response element region comprises:

(i) the sequence $N_4$TTTCTAGGAATN$_5$ (SEQ ID NO: 25); wherein $N_4$ is a sequence of four nucleotides independently selected from A, T, C, or G and $N_5$ is a sequence of five nucleotides independently selected from A, T, C, or G; or (ii) a sequence complementary to the sequence in (i).

In certain embodiments, a response element region comprises:

(a) the sequence $E_3$ or a sequence complementary to the sequence $E_3$;

(b) the sequence $E_3$-X-$E_3$ or a sequence complementary to the sequence $E_3$-X-$E_3$;

(c) the sequence $E_3$-X-$E_3$-Y-$E_3$ or a sequence complementary to the sequence $E_3$-X-$E_3$-Y-$E_3$; or (d) the sequence $E_3$-X-$E_3$-Y-$E_3$-Z-$E_3$ or a sequence complementary to the sequence $E_3$-X-$E_3$-Y-$E_3$-Z-$E_3$;

wherein Y, X, and Z are each independently selected from a nucleic acid sequence of 0 to 48 (including any integer within that range) nucleotides, and wherein $E_3$ is $[N_5$TTCCQGGAAN$_6]_3$ (SEQ ID NO: 26); $[N_4$TTTCCQGGAAAN$_5]_3$ (SEQ ID NO: 27); $[N_4$TTTCCCCGAAAN$_5]_3$ (SEQ ID NO: 28); $[N_4$ATTCTCAGAAAN$_5]_3$ (SEQ ID NO: 29); or $[N_4$TTTCTAGGAATN$_5]_3$ (SEQ ID NO: 30); wherein Q is the nucleotide A, C, or T; $N_4$ is a sequence of four nucleotides independently selected from A, T, C, or G; $N_5$ is a sequence of five nucleotides independently selected from A, T, C, or G; and $N_6$ is a sequence of six nucleotides independently selected from A, T, C, or G.

In certain embodiments, Y, X, and/or Z may serve as spacer elements to provide space between multiple triple repeat sequences. In certain embodiments, a spacer element is a multiple of 10 to 12 nucleotides long, which results in the center regions of each repeat sequence being spatially oriented to be in approximately the same location (on the y and z axis) plus or minus 36 degrees, relative to the center axis of the double-helical DNA (x-axis), wherein the center region is the middle two nucleotides of the particularly recited sequence. In certain embodiments, a spacer element is 10 to 12 nucleotides long. In certain embodiments, a spacer element is 20 to 24 nucleotides long. In certain embodiments, a spacer element is 23 nucleotides long. In certain embodiments, a spacer element is 30 to 36 nucleotides long. In certain embodiments, a spacer element is 8 to 12 nucleotides long. In certain embodiments, a spacer element is 16 to 24 nucleotides long. In certain embodiments, a spacer element is 24 to 36 nucleotides long.

In certain embodiments, Y, X, and/or Z may serve a functional role in transcription. For example, in certain embodiments, transcription factors may bind to Y, X, and/or Z. Exemplary transcription factors that may bind may bind to Y, X, and/or Z, include, but are not limited to, NFAT, AP-1, CRE, NFκB, and members of the STAT protein family.

In certain embodiments, a response element region contains more than one set of sequences that bind at least one STAT protein. In certain such embodiments, each set of sequences that bind at least one STAT protein is embedded in the center of a twenty (20)-mer, where the sequences flanking the set of sequences that bind at least one STAT protein can be any nucleotides A, T, C, or G to complete the twenty-mer. Certain STAT protein binding sites are disclosed in PCT Publication No. WO 95/28482.

In certain embodiments, a reporter nucleic acid construct is provided. Various reporter nucleic acid constructs comprise various components in addition to a response element region.

In certain embodiments, a response element region is operably linked to a promoter. In certain embodiments, a promoter is capable of being bound directly or indirectly by a polymerase, which results in transcription of a downstream encoding sequence. Many different promoters may be used according to various embodiments. In various embodiments, promoters may be eukaryotic, prokaryotic, or viral promoters that are capable of driving transcription of an encoding sequence when transfected into a host cell.

One skilled in the art will be able to determine suitable promoters for use in a given reporter nucleic acid construct and a given host cell. Nonlimiting exemplary promoters include, but are not limited to, SV40 promoter, thymidine kinase (TK) promoter, PGK promoter, beta actin promoter, CMV promoter, RSV promoter, MSCV promoter, MuLV promoter, HIV promoter, and polyhedron promoter, and fragments and minimal promoters based on any of these promoters. Nonlimiting exemplary promoters are described, e.g., in PCT Publication No. WO 95/28482.

In certain embodiments, a reporter nucleic acid construct comprises a reporter nucleic acid, which encodes a polypeptide that can be used to detect expression of the reporter nucleic acid. Many different reporter nucleic acids may be used according to various embodiments. The polypeptide expressed by a reporter nucleic acid (reporter polypeptide) may be detected directly or indirectly.

In certain embodiments, a reporter polypeptide may be detected by using a molecule that binds to the reporter polypeptide. In various embodiments, the molecule that binds the reporter polypeptide may be any molecule that has affinity for the reporter polypeptide. In certain embodiments, the molecule that binds the reporter polypeptide is labeled. In certain embodiments, the molecule that binds to the reporter polypeptide is an antibody. In certain embodiments, a reporter polypeptide may be detected by its interaction with another molecule. In certain embodiments, the reporter polypeptide is an enzyme that interacts with another molecule to provide a signal.

Nonlimiting exemplary reporter polypeptides include, but are not limited to, fluorescent molecules, chemilluminescent molecules, electrochemillunescent molecules, luciferase (LUC), phosphatase, alkaline phosphatase, placental alkaline phosphatase, beta-galactosidase, green fluorescent protein, beta-lactamase. Nonlimiting exemplary reporter polypeptides are described, e.g., in PCT Publication No. WO 95/28482.

In certain embodiments, a reporter nucleic acid construct is used to test the activity of a signaling molecule and/or the ability of a test compound to affect the activity of a signaling molecule. As discussed above, a signaling molecule refers to an extracellular molecule, in either a free or bound form, that interacts with a receptor of a cell, which triggers a process that affects the activity of one or more response element transcription factor. Many different signaling molecules may be used according to various embodiments. In certain embodiments, a signaling molecule interacts with a receptor of a cell, which triggers a process that activates one or more response element transcription factor. In certain embodiments, a signaling molecule interacts with a receptor of a cell, which triggers a process that deactivates one or more response element transcription factor. In certain embodiments, activation of one or more response element transcription factor results in binding of the one or more activated response element transcription factor to a response element region, which results in expression of a reporter nucleic acid.

Exemplary signaling molecules include, but are not limited to, polypeptides, oligosaccharides, small organic molecules, antibodies, peptibodies, carbohydrates, peptide mimetics, fusion proteins, complex organic molecules (including, but not limited to, steroids), and lipids (including, but not limited to, phospholipids). In certain embodiments, a signaling molecule is a cytokine. In certain embodiments, a signaling molecule is a growth factor. Nonlimiting exemplary signaling molecules are described, e.g., in PCT Publication No. WO 95/28482. In certain embodiments, more than one signaling molecule may be involved in a process of modulating response element transcription factor activity.

In certain embodiments, a signaling molecule interacts with a receptor of a cell, which triggers a process that results in activation of STAT5. Exemplary signaling molecules that have been shown to be involved in triggering such a process in certain instances include, but are not limited to, Interleukin (IL)-1, IL-2, IL-3, IL-4, IL-5, IL-7, IL-9, IL-10, IL-12, IL-13, IL-15, IL-15, IL-27, erythropoietin (EPO), tPO, G-CSF, GM-CSF, growth hormone, TSLP, cKit, erythropoeitic products, GCSF-like molecules, and prolactin. Exemplary signaling molecules include, but are not limited to: naturally occurring polypeptides; polypeptides that have a naturally occurring amino acid sequence; polypeptides that have an amino acid sequence that is 70%, 80%, 85%, 90%, 95%, 96%, 97%, 98%, or 99% identical to a naturally occurring amino acid sequence; fusion proteins that comprise at least one naturally occurring amino acid sequence; chemically modified polypeptides; polypeptides with a polymer attached, e.g., polyethylene glycol (PEG); and molecules that have the signaling molecule activity of a naturally occurring polypeptide.

The term "G-CSF" as used herein is defined as naturally occurring human and heterologous species granulocyte colony-stimulating factor, recombinantly produced granulocyte colony-stimulating factor that is the expression product consisting of either 174 or 177 amino acids, or fragments, analogs, variants, or derivatives thereof, such as (recombinant methionyl human granulocyte colony-stimulating factory), and as reported, for example in Kuga et al., Biochem. Biophys. Res. Comm. 159: 103-111 (1989); Lu et al., Arch. Biochem. Biophys. 268: 81-92 (1989); U.S. Pat. Nos. 4,810, 643, 4,904,584, 5,104,651, 5,214,132, 5,218,092, 5,362,853, 5,606,024, 5,824,778, 5,824,784, 6,017,876, 6,166,183, and 6,261,550; U.S. Pat. Appl. No. US 2003/0064922; EP 0335423; EP 0 272703; EP 0 459630; EP 0 256843; EP 0 243153; WO 9102874; Australian Application document Nos. AU-A-10948/92 and AU-A-76380/91. Included are chemically modified granulocyte colony-stimulating factors, see, e.g., those reported in WO 9012874, EP 0401384 and EP 0335423. See also, WO 03006501; WO 03030821; WO 0151510; WO 9611953; WO 9521629; WO 9420069; WO 9315211; WO 9305169; JP 04164098; WO 9206116; WO 9204455; EP 0473268; EP 0456200; WO 9111520; WO 9105798; WO 9006952; WO 8910932; WO 8905824; WO 9118911; and EP 0 370205. Also encompassed herein are all forms of granulocyte colony-stimulating factor, such as Albugranin™, Neulasta™, Neupogen®, and Granocyte®.

Derivatives of G-CSF include molecules modified by one or more water soluble polymer molecules, such as polyethylene glycol, or by the addition of polyamino acids, including fusion proteins (procedures for which are well-known in the art). Such derivatization may occur singularly at the N- or C-terminus or there may be multiple sites of derivatization. Substitution of one or more amino acids with lysine may provide additional sites for derivatization. (See U.S. Pat. No. 5,824,784 and U.S. Pat. No. 5,824,778, incorporated by reference herein).

The term "G-CSF-like molecules" means a molecule that can activate the STAT protein through the granulocyte colony-stimulating factor receptor or portions thereof.

As meant herein, the term "erythropoietic product" means a product that can activate the STAT protein through the erythropoietin receptor or portions thereof. An erythropoietic product comprises an "erythropoietic glycoprotein" (as defined herein), which glycoprotein can be conjugated to a non-protein molecule. An erythropoietic product as used herein includes naturally occurring human and hereologous species erythropoietin, recombinantly-produced erythropoietin, such as Epogen® (epoietin alfa), Aranesp® (darbepoetin alfa), biologically active precursors, mimetics, analogs, variants, or derivatives thereof as reported, for example in U.S. Pat. Nos. 6,586,398, 6,319,499, 5,955,422, 5,856,298, 5,441, 868, 4,703,308, WO 91/05867, WO 95/05465, and WO 96/40749 (all incorporated by reference herein).

An erythropoietic glycoprotein is preferably a secreted, recombinant protein. Included among these erythropoietic products are erythropoietic glycoproteins that have been chemically modified, for example an erythropoietin glycoprotein conjugated to polyethylene glycol, such as those disclosed in International Application Nos. WO 01/02017 and WO 01/76640, U.S. Pat. Nos. 6,077,939, 5,643,575, 6,340, 742, US Patent Application No. 2002/0115833, and European Patent No. 1 064 951 (all included by reference herein). Further, an erythropoietic product can be a composition that comprises an erythropoietic glycoprotein and, optionally, one or more additional components such as a physiologically acceptable carrier, excipient, or diluent. For example, a composition may comprise an erythropoietic glycoprotein as described herein plus a buffer, an antioxidant such as ascorbic acid, a low molecular weight polypeptide (such as those having less than 10 amino acids), a protein, amino acids, carbohydrates such as glucose, sucrose, or dextrins, chelating agent such as EDTA, glutathione, and/or other stabilizers, excipients, and/or preservatives. The composition may be formulated as a liquid or a lyophilizate. Further examples of components that may be employed in pharmaceutical formulations are presented in Remington's Pharmaceutical Sciences, 16$^{th}$ Ed., Mack Publishing Company, Easton, Pa., (1980). Further, the term "erythropoietic products" includes solutions or formulations comprising the erythropoietic glycoproteins described below, which may have enhanced stability and/or activity, such as those described in U.S. Pat. Nos. 4,806,524, 6,333,306, and 6,277,367 (all incorporated by reference herein).

As meant herein, the term "erythropoietic glycoprotein" encompasses glycoproteins that have the same amino acid sequence as any mammalian erythropoietin glycoprotein, including human erythropoietin, as well as analogs and variants of each, i.e., erythropoietic glycoprotein analogs and erythropoietic glycoprotein variants. Human erythropoietin sequences are disclosed in U.S. Pat. Nos. 4,703,008 and 5,688,679, European Patent No. 0 205 564, and International Application No. WO 02/085940 (all incorporated herein by reference). Primate erythropoietin sequences are disclosed in, e.g., U.S. Pat. Nos. 4,703,008 and 6,555,343 and National Center for Biotechnology Information (NCBI) accession no. AAA36842, and other mammalian erythropoietins are disclosed in, for example, International Application No WO 99/54486 (canine erythropoietin), NCBI accession nos. AAA37570 (mouse erythropoietin), AAA30842 (canine erythropoietin), AAA30807 (cat erythropoietin), and AAA31029 (pig erythropoietin), among many other published mammalian erythropoietin sequences (all incorporated herein by reference). Erythropoietic glycoproteins produced and/or purified by methods described in U.S. Pat. Nos. 4,667,016, 6,399,333, 6,391,633, and 6,355,241 (all incorporated herein by reference) are erythropoietic glycoproteins as meant herein.

Specifically included within "erythropoietic glycoprotein analogs" are glycoproteins that are substantially similar to a mammalian erythropoietin and that can stimulate erythropoiesis as demonstrated in an in vivo bioassay, for example, the exhypoxic polycythemic mouse assay. See e.g. Cotes and Bangham (1961), Nature 191: 1065. Examples of erythropoietic glycoprotein analogs include the analogs described in International Application Nos. WO 95/05465 and WO 01/81405 (incorporated herein by reference) which provide analogs of human erythropoietin comprising more N-glycan sites than are present in unaltered human erythropoietin. For example, the analog designated N47 in WO 95/05465 comprises five N-glycan sites, and the analog designated N66 in WO 01/81405 comprises seven N-glycan sites rather than the three present in unaltered human erythropoietin. Other erythropoietic glycoprotein analogs include those comprising any single alteration described in International Application Nos. WO 95/05465 and/or WO 01/81405 or any combination of such alterations, provided that the resulting protein is still substantially similar to human erythropoietin. Other examples include the erythropoietic glycoprotein analogs disclosed in U.S. Pat. Nos. 5,856,298 and 6,153,407, International Application Nos. WO 00/24893, WO 91/05867, and WO 00/24893, and WO 03/029291, and European Patent Application 0 902 085 (all herein incorporated by reference). One such erythropoietic glycoprotein analog has been given the United States Adopted Name (USAN) darbepoetin alfa and is marketed under the tradename ARANESP® by Amgen Corporation of Thousand Oaks, Calif., USA. Still other erythropoietic glycoprotein analogs include human erythropoietin with an additional amino acid at the carboxy-terminus, for example arginine.

Included among "erythropoietic glycoprotein variants" are molecules comprising an erythropoietic glycoprotein analog, as defined above, a mammalian erythropoietin, or a fragment either of these that can stimulate erythropoiesis fused to a different protein, polypeptide, or fragment thereof. Erythropoietin variants include the fusion proteins described in, e.g., U.S. Pat. No. 6,548,653, among many others such as variants including the Fc region of an antibody or a dimerization or trimerization domain, for example a leucine zipper.

Human erythropoietin is 165 amino acids long and has three N-glycan sites that allow attachment of N-glycans at amino acids 24, 38, and 83 and one O-glycan site that allows attachment of an O-glycan at amino acid 126. This protein is described in U.S. Pat. No. 4,703,008, where it is described by amino acids 1 to 165 in FIG. 6. An analog of human erythropoietin, N47, which is produced by cells used in Examples 1, 2, and 4, is also 165 amino acids long and has five N-glycan sites that allow attachment of N-glycans at amino acids 24, 30, 38, 83, and 88 and one O-glycan site that allows attachment of an O-glycan at amino acid 126. This protein is described in International Application No. WO 95/05465, where it is designated analog "N47."

In certain embodiments, a signaling molecule interacts with a receptor of a cell, which triggers a process that results in activation of one or more STAT protein other than STAT5. In certain embodiments, a signaling molecule interacts with a receptor of a cell, which triggers a process that results in activation of one or more response element transcription factor other than a STAT protein.

In certain embodiments, a signaling molecule-responsive host cell is provided. Many different signaling molecule-responsive host cells may be used according to various embodiments. As discussed above, a signaling molecule-responsive host cell refers to a host cell that comprises a signaling molecule receptor cabable of interacting with a signaling molecule. In certain embodiments, a signaling molecule receptor is capable of interacting with a signaling molecule described above. In certain embodiments, a signaling molecule receptor is a cytokine receptor. In certain embodiments, a signaling molecule receptor is a growth factor receptor. Nonlimiting exemplary signaling molecule receptors are described, e.g., in PCT Publication No. WO 95/28482.

In certain embodiments, a signaling molecule receptor is capable of interacting with a signaling molecule, which triggers a process that results in activation of STAT5. Exemplary signaling molecule receptors involved in triggering such a process in certain instances include, but are not limited to, Interleukin (IL)-1 receptor, IL-2 receptor, IL-3 receptor, IL-4 receptor, IL-5 receptor, IL-7 receptor, IL-9 receptor, IL-10 receptor, IL-12 receptor, IL-13 receptor, IL-15 receptor, IL-15 receptor, IL-27 receptor, Epo receptor, tPO receptor, G-CSF receptor, GM-CSF receptor, growth hormone receptor, TSLP receptor, cKit receptor, and prolactin receptor.

In certain embodiments, a signaling molecule receptor is capable of interacting with a signaling molecule, which triggers a process that results in activation of one or more STAT protein other than STAT5. In certain embodiments, a signaling molecule receptor is capable of interacting with a signaling molecule, which triggers a process that results in activation of one or more response element transcription factor other than a STAT protein.

In certain embodiments, a signaling molecule receptor is a chimeric signaling molecule receptor. In certain embodiments, a chimeric signaling molecule receptor comprises a molecule comprising at least two portions from different receptor molecules. A nonlimiting exemplary chimeric signaling molecule receptor molecule is a molecule comprising at least a portion of the extracellular domain of the Epo receptor and at least a portion of the cytoplasmic domain of prolactin receptor. See, e.g., Socolovsky et al., Journal of Biological Chemistry, 272(22):14009-14012 (1997).

In certain embodiments, a signaling molecule-responsive host cell expresses a signally molecule receptor from an endogenous gene. In certain embodiments, a signaling molecule-responsive host cell expresses from an endogenous gene one or more response element transcription factor, whose activity is affected by the interaction of a signaling molecule receptor and a signaling molecule. In certain embodiments, a signaling molecule-responsive host cell expresses a signaling molecule receptor from an endogenous gene, and expresses from an endogenous gene one or more response element transcription factor, whose activity is affected by the interaction of the signaling molecule receptor and a signaling molecule. This discussion of expressing a signaling molecule receptor encompasses host cells that express more than one type of signaling molecule receptor.

In certain embodiments, a signaling molecule-responsive host cell expresses one or more signaling molecule receptors from one or more exogenous nucleic acids. In certain embodiments, the signaling molecule-responsive host cell expresses one or more response element transcription factors from one or more exogenous nucleic acids. In certain embodiments, one or more exogenous nucleic acids have been transiently introduced into the host cell. In certain embodiments, one or more exogenous nucleic acids have been stably introduced into the host cell. In various embodiments, a nucleic acid that can express a signaling molecule receptor and can express one or more response element transcription factor has been introduced into a signaling molecule-responsive host cell by any method known in the art. In certain embodiments, a nucleic acid that can express a signaling molecule receptor and a separate nucleic acid that can express one or more response element transcription factor have been introduced into a signaling molecule-responsive host cell.

In certain embodiments, a signaling molecule-responsive host cell may express a signaling molecule receptor from an endogenous gene, but to increase the amount of receptor, the host cell also expresses the signaling molecule receptor from an exogenous nucleic acid. In certain embodiments, a host cell may not express a signaling molecule receptor from an endogenous gene, and the host cell expresses the signaling molecule receptor from an exogenous nucleic acid. This discussion of a host cell that expresses a signaling molecule receptor encompasses host cells that express more than one type of signaling molecule receptor from an exogenous nucleic acid.

In certain embodiments, a host cell may express one or more response element transcription factors from an endogenous gene, but to increase the amount one or more response element transcription factor, the host cell also expresses one or more response element transcription factor from an exogenous nucleic acid. In certain embodiments, a host cell may not express one or more response element transcription factor from an endogenous gene, and the host cell expresses one or more response element transcription factor from an exogenous nucleic acid. This discussion of a host cell that expresses one or more response element transcription factor encompasses host cells that express one or more response element transcription factor from more than one exogenous nucleic acid.

Exemplary host cells that may transfected with a reporter nucleic acid construct include, but are not limited to, NIH-3T3 fibroblast cells, UT7 cells, BaF3 cells, 32D clone 3 cells, 32D clone 23 cells, DA-1 cells, DA-3 cells, A431 cells, C3H10T1/2 cells, CaCo 2 cells, CHO cells, COS-7 cells, CV-1 cells, Daudi cells, Jurkat cells, EL-4 cells, Hela cells, HEK293 cells, HUVEC cells, HL-60 cells, U937 cells, HepG2 cells, HT1080 cells, HUT78 cells, L cells, MC/9 cells, RBL-1 cells, MO7e cells, Neuro 2A cells, PC-12 cells, RAJI cells, Ramos cells, Rat-1 cells, Saos-2 cells, ST-2 cells, THP-1 cells, TF1 cells, Wehi-3 cells, bone marrow cells, CD34 positive cells, embryonic stem cells, and germ cells. Nonlimiting exemplary host cells are described, e.g., in PCT Publication No. WO 95/28482.

UT7/Epo cells naturally comprise Epo receptors. Accordingly, in certain embodiments, UT7/Epo cells transfected with a reporter nucleic acid construct may be used to test Epo activity. BaF3 cells naturally comprise IL-3 receptors. Accordingly, in certain embodiments, BaF3 cells transfected with a reporter nucleic acid construct may be used to test IL-3 activity.

In certain embodiments, 32D clone 3 cells are transfected with a nucleic acid that expresses human G-CSF receptor and with a reporter nucleic acid construct. Accordingly, in certain embodiments, such transfected cells can be used to test G-CSF activity. In certain embodiments, NIH-3T3 cells are transfected with a nucleic acid that expresses Epo receptor and with a reporter nucleic acid construct. Accordingly, in certain embodiments, such transfected cells can be used to test Epo activity.

Certain Exemplary Methods

In certain embodiments, a signaling molecule-responsive host cell comprising a reporter nucleic acid construct may be used to determine the activity of a test composition comprising a signaling molecule. In certain embodiments, the signaling molecule-responsive host cell comprising a reporter nucleic acid construct is contacted with the test composition under conditions in which the reporter nucleic acid construct expresses a reporter polypeptide in response to the signaling molecule. If the test composition contains a sufficient amount of the active signaling molecule, reporter polypeptide will be produced at a level that can be detected.

As a non-limiting example, a signaling molecule-responsive host cell may be transformed or transfected, either stably or transiently, with a reporter nucleic acid construct that comprises at least a response element region, a promoter, and a reporter nucleic acid in operable combination. If the reporter nucleic acid is a luciferase gene, for example, then contacting the signaling molecule-responsive host cell comprising the reporter nucleic acid construct with a test composition comprising the signaling molecule will result in expression of luciferase, which may be detected using an appropriate assay and a luminometer. The amount of light produced may be directly related to the amount of luciferase protein expressed from the reporter nucleic acid construct, which in turn may be related to the amount of signaling molecule activity present in the test composition.

In certain embodiments, the test composition comprising a signaling molecule is a particular production batch of the signaling molecule. In certain embodiments, a production batch of the signaling molecule is produced by expressing a recombinant gene for the signaling molecule in prokaryotic or eukaryotic cells. In certain embodiments, the signaling molecule is further purified to produce a production batch. In certain embodiments, a production batch of the signaling molecule is produced by purifying the signaling molecule from cells that express the signaling molecule from an endogenous gene. A production batch includes batches suitable for experimental purposes as well as batches suitable for large-scale production of pharmaceutical molecules. Thus, a production batch may be of any size.

In certain embodiments, the test composition may be a composition comprising a sample suspected of containing the signaling molecule. Non-limiting exemplary samples include mammalian tissues and mammalian samples, including, but not limited to, blood, urine, serum, saliva, muscle, bone marrow, thymus, spleen, kidney, liver, adrenal gland, brain, spinal fluid, peritoneal fluid, and bronchial lavage. Non-limiting exemplary samples also include, but are not limited to, plant tissues and cells, non-mammalian eukaryotic tissues and cells, prokaryotic cells, medium that has been in contact with cells, and any of the above sources upon introduction of specific conditions, e.g., varying nutrients and/or stress levels. In certain embodiments, the sample is from a nonbiological origin, for example from a chemical synthesis. Samples may be manipulated as appropriate, e.g., by extraction, solubilization, filtration, dilution, etc., in order to form a test composition. One skilled in the art can form an appropriate test composition from a particular sample.

The activity of the test composition comprising a signaling molecule may, in certain embodiments, be compared to the activity of a standard composition comprising the signaling molecule subjected to the same assay. A standard composition comprising the signaling molecule may, in certain embodiments, comprise a known concentration of the signaling molecule (e.g., the standard composition may comprise x mg/mL or y mmol/mL of the signaling molecule). In certain embodiments, a standard composition comprising the signaling molecule may comprise a known concentration of signaling molecule activity (e.g., the standard composition may comprise z units of activity/mL). In certain embodiments, a standard composition comprising the signaling molecule may comprise a known concentration of the signaling molecule and a known concentration of signaling molecule activity (e.g., the standard composition may comprise x mg/mL of signaling molecule and z units of activity/mL of signaling molecule activity, which means that the signaling molecule in the standard composition has z units of activity per x mg of signaling molecule).

In certain embodiments, by comparing the activity of a test composition comprising a signaling molecule to a standard composition comprising the signaling molecule, one skilled in the art may adjust the concentration of the signaling molecule in the test composition or the concentration of signaling molecule activity in the test composition as desired. In certain embodiments, the concentration of the signaling molecule in the test composition or the concentration of the signaling molecule activity in the test composition is adjusted to be the same as that of the standard composition.

In certain embodiments, the activity of the test composition comprising a signaling molecule may be compared to the activity of a blank composition that lacks the signaling molecule subjected to the same assay. The activity of the test composition comprising the signaling molecule may, in certain embodiments, be expressed as a "fold-stimulation" over the activity of the blank composition. Fold-stimulation may be calculated, in certain embodiments, by dividing the signal of the test composition by the signal of the blank composition in the same assay. In certain embodiments, a background signal is subtracted from the signal of each test composition before calculating the fold-stimulation. In various embodiments, the background signal may be, e.g., the signal produced by the assay reagents without any cells, the signal produced by the signaling molecule-responsive cells lacking the reporter nucleic acid construct, or any other appropriate background measure.

In certain embodiments, a signaling molecule-responsive host cell comprising a reporter nucleic acid construct may be used to determine whether a test compound has the activity of a particular signaling molecule. In certain embodiments, the signaling molecule-responsive host cell comprising a reporter nucleic acid construct is contacted with the test compound, in the absence of the signaling molecule, under conditions in which the reporter nucleic acid construct expresses a reporter protein in response to the signaling molecule. If the test compound has the activity of the signaling molecule, reporter protein will be produced at a level that can be detected.

In certain embodiments, a test compound that has the activity of a particular signaling molecule is referred to as an "agonist." Agonists include any molecule that results in the specific downstream effects that are characteristic of a particular signaling molecule. Thus, as used herein, an agonist is any molecule that, when contacted with a certain signaling molecule-responsive host cell comprising a certain reporter nucleic acid construct, results in expression of the reporter polypeptide. An agonist need not function by the same mechanism as the signaling molecule. Thus, as a non-limiting example, an agonist need not bind the signaling molecule's cognate receptor in the same location or manner as the signaling molecule, and indeed, the agonist need not bind the receptor at all.

In certain embodiments, the activity of a test compound that may have the activity of a particular signaling molecule is compared to the activity of a standard composition comprising the signaling molecule. One skilled in the art can select a test compound that has the desired level of activity relative to a standard composition.

In certain embodiments, the activity of a test compound that may have the activity of a particular signaling molecule is compared to the activity of a blank composition that lacks the signaling molecule. In certain embodiments, the activity of the test compound may be expressed as a fold-stimulation over the blank composition, substantially as discussed above.

In certain embodiments, a library of test compounds may be tested to select compounds having the activity of a particular signaling molecule. In certain embodiments, the assays discussed herein may be adapted by methods known in the art for high-throughput screening of a library comprising a large number of such test compounds.

In certain embodiments, a signaling molecule-responsive host cell comprising a reporter nucleic acid construct may be used to determine whether a test compound impacts the activity of a signaling molecule. In certain embodiments, the signaling molecule-responsive host cell comprising a reporter nucleic acid construct is contacted with the signaling molecule and the test compound under conditions in which the reporter nucleic acid construct expresses a reporter protein in response to the signaling molecule. In certain embodiments, the activity of the signaling molecule alone is compared to the activity of the signaling molecule in the presence of the test compound under the same assay conditions. If the test compound impacts the activity of the signaling molecule, the level of reporter protein produced will be different from the level of reporter protein produced in the presence of the signaling molecule alone.

In certain embodiments, a test compound that specifically inhibits the activity of a signaling molecule is referred to as an "inhibitor." Thus, an inhibitor includes any molecule that specifically reduces the level of reporter protein expressed in response to the signaling molecule. The inhibitor's mechanism of action is not limited. Thus, an inhibitor may reduce the activity of a signaling molecule by any mechanism, including, but not limited to, preventing or reducing signaling molecule binding to its cognate receptor, preventing or reducing phosphorylation of any protein or proteins in the signaling pathway, and/or preventing or reducing activated response element transcription factor binding to the reporter nucleic acid construct.

In certain embodiments, a test compound may specifically increase the activity of a signaling molecule. The mechanism of such an increase is not limited. Thus, a test compound that specifically increases the activity of a signaling molecule may function by any mechanism, including, but not limited to, mimicking the binding of the signaling molecule to its cognate receptor, increasing and/or stabilizing the binding of the signaling molecule to its cognate receptor, increasing the extent and/or rate of phosphorylation of any protein or proteins in the signaling pathway, and/or increasing the level and/or stability of activated response element transcription factor binding to the reporter nucleic acid construct.

In certain embodiments, a response element region may be operably linked to a promoter, which is operably linked to a gene of interest. A nucleic acid comprising the response element region operably linked to a promoter, which is operably linked to a gene of interest is referred to herein as an inducible nucleic acid construct. In certain embodiments, incubation of a host cell comprising an inducible nucleic acid construct with a signaling molecule results in expression of the gene of interest. In that manner, in certain embodiments, expression of the gene of interest may be controlled by varying the concentration of signaling molecule in contact with the host cell. In certain embodiments, cells comprising the inducible nucleic acid construct may be grown to a desired density in the absence of the signaling molecule, and then signaling molecule may be added to induce expression of the gene of interest. Such a system may be useful, in certain embodiments, for producing a polypeptide product of a gene of interest, where that polypeptide product reduces the growth and/or is toxic to the host cells. Such a system may also be useful, in certain embodiments, when the gene of interest is be activated, e.g., at a certain time point, at a certain cell density, or after certain other events have occurred.

Methods of producing proteins or polypeptides are known to one of skill in the art. One example is the production of erythropoietin as described in U.S. Pat. No. 5,441,868. One of skill in the art would know how to produce proteins from bacterial, mammalian systems in vivo, ex vivo, or in vitro.

EXAMPLES

Example 1

Making pGLGTPLAP

A double-stranded nucleic acid having the following nucleic acid sequence was cloned into pBlueScript® (Stratagene) cut with Asp718+SacII to yield pBlue A/S:

5' CGTCATTTCCAGGAAATCA CCGTCATTTCCAG-GAAATCA CCGTCATTTCCAG

3' CAT GGCAGTCCCGGTCCTTTAGT GGCAGTAAAG-GTCCTTTAGT GGCAGTAAAGGTC
GAAATCA CCGC 3' (SEQ ID NO: 31)
CTTTAGT GG 5' (SEQ ID NO: 32)

Both strands are shown, including the overhangs generated for cloning. Bold indicates a response element repeat sequence. A double-stranded nucleic acid having the following nucleic acid sequence was cloned into pBlueScript® cut with SacII+HindIII to yield pBlue H/S:

5' GGTCCCAGGTCCACTTCGCATATTAAG-GTGACGCGTGTGGCCTCGAACACC A 3' (SEQ ID NO: 33)

3'C GCCAGGGTCCAGGTGAAGCGTATAATTC-CACTGCGCACACCGGAGCTTGTGG TTCGA 5'(SEQ ID NO: 34)

Both strands are shown, including the overhangs generated for cloning. Underlining indicates a TK promoter sequence.

The Asp718-SacII and SacII-HindIII fragments were released from pBlue A/S and pBlue H/S, respectively, and were cloned into Asp718+HindIII cut pGL3Basic (Promega) in a three-part ligation to yield pGTbasic, which comprised the following sequence:

GTA CCGTCATTTCCAGGAAATCA CCGTCATTTC-CAGGAAATCACCGTCATTTCC AGGAAATCA CCGCGGTCCCAGGTCCACTTCGCATAT-TAAGGTGACGCGTGTGGC CTCGAACACC AAGCT (SEQ ID NO: 35)

(Only one strand is shown. Italicized sequences indicate parts of the restriction sites used for cloning. Bold indicates a response element repeat sequence and underlining indicates a TK promoter sequence).

Construct pGLGFP was made by ligating the 250 base-pair NotI (filled in)-NcoI fragment from pGL3Basic into BgIII cut (filled in) pEGFP (Clontech).

The 120 base-pair Asp718-HindIII (1×GAS-TKpromoter) fragment was released from pGTbasic (discussed above) and ligated into Asp718-HindIII cut pGLGFP to yield pGLGT-GFP.

PLAP-76-SEQSIG comprises a human placental alkaline phosphatase (PLAP) cDNA with an artificially constructed N-terminus, including a secretion signal sequence, and lacking the C-terminal glycosylphosphatidyl inositol (GPI) anchor sequence. Specifically, the PLAP sequence in PLAP-76-SEQSIG comprises the following 5' nucleotide sequence, which includes the artificially constructed N-terminus fused to nucleotides 102 to 1571 of the PLAP sequence shown in Genbank® # M13077:

5' T CTAGACTCGA CATGCTGGGG CCCTGCATGC TGCTGCTGCT GCTGCTGCTG GGCCTGAGGC TACAGCTCTC CCTGGGCATC ATCGCGGCCG CAG-GCATCAT 3' (SEQ ID NO: 36)

Only one strand is shown. The XbaI sequence at the 5' end of the region shown is underlined. The nucleotide sequence encoding the artificially-constructed N-terminus, including a secretion signal sequence, is in bold. Part of the native PLAP sequence beginning at nucleotide 102 of Genbank® #M13077 is shown in italics. At the 3' end of the PLAP insert in PLAP-76-SEQSIG is the following sequence:

5' GCGCACCCGG GGGCTAGCTA AGGTACC 3' (SEQ ID NO: 37)

Only one strand is shown. The italicized portion is part of the native PLAP sequence to nucleotide 1571 of Genbank®# M13077. The stop codon is shown in bold and the Asp718 site is underlined.

Blunt-ended 1.5 Kb XbaI-Asp718 fragment from PLAP-76-SEQSIG, which includes the artificially constructed N-terminal signal sequence, nucleotides 102-1571 of human PLAP (Genbank® # M13077), and the stop codon, was ligated into blunt-ended HindIII-NotI cut pGLGTGFP to yield pGLGTPLAP.

Self-annealed double stranded nucleic acid 1596-13 (CG-TACGGC) was ligated into SacII-cut pGTbasic to create a BsiWI site and yield p1596-13/GTbasic comprising the following sequence:
GTA CCGTCATTTCCAGGAAATCA CCGTCATTTC-CAGGAAATCA CCGTCATTTCCAGGAAATCA CCG ccgtacgg CGGTCCCAGGTCCACTTCGCATATTAAG-GTGACGCGTGTGGCCTCG AACACC AAGCT (SEQ ID NO: 38)
(Only one strand is shown. Bold indicates a response element repeat sequence, underlining indicates a TK promoter sequence, and the lower case sequence indicates nucleotides added by nucleic acid 1596-13).

The Asp718-BsiWI fragment from p1596-13/GTbasic was released and ligated into Asp718 cut pGLGTPLAP to generate a multi-GT-PLAP mixture (3× response element repeat sequence; 6× response element repeat sequence, 9× response element repeat sequence, 12× response element repeat sequence, >12× response element repeat sequence).

For example, a 9× Multi-GT-PLAP, comprises the following sequence: 1 GCAAGTGCAGGTGCCAGAA-CATTTCTCTATCGATAG GTA CCGTCATTTCCAG-GAAATCA CCGTCATTTCCAGGAAATCA CCGTCATTTCCAGGAAATCA CCG ccgta CCGT-CATTTCCAGGAAATCA CCGTCATTTCCAG-GAAATCA CCGTCATTTCCAGGAAATCA CCG ccgta CCGTCATTTCCAGGAAATCA CCGTCATTTCCAG-GAAATCA CCGTC ATTTCCAGGAAATCA CCG CGGTCCCAGGTCCACTTCGCATATTAAGGTGA CGCGTGTGGCCTCGAACACC AAGCT CTAGACTC-GACATGCTGGGGCCCTGCATG (SEQ ID NO: 39)

Example 2

Testing with EPO pGTPLAP DNAs with three (9× response element repeat sequence) or four (12× response element repeat sequence) copies of the response element triple repeat sequence were individually purified and linearized with ApaL1 for transient transfection into NIH-3T3 fibroblasts (3×10e5 cells/well) following standard procedures using Superfect™ (Qiagen) as transfection reagent and DMEM basal medium. The pGT-PLAP constructs were transfected into NIH-3T3 fibroblast cells alone or in various combinations with an expression plasmid for the Epo Receptor and/or an expression plasmid for STAT5b (Azam et al, EMBO J, 14(7), 1402-1411, 1995). The expression plasmid for the Epo Receptor was an MSCV retroviral expression vector into which human full length Epo Receptor had been cloned. See Hawley et al., Gene Therapy, 1:136-138 (1994) for the MSCV retroviral expression vector and GenBane® Accession No. 60459 for human Epo Receptor. Also, NIH-3T3 fibroblast cells were transfected with only the expression plasmid for the Epo Receptor. Also, NIH-3T3 fibroblast cells were transfected with only the expression plasmid for STAT5b. Also, nontransfected NIH-3T3 fibroblast cells were used. Table 1 below shows the various combinations that were tested. After a 2-3 hour incubation with the DNA-transfection mix, cells were washed with PBS and placed in fresh 3T3 growth medium (phenol red-free DMEM, 10% FBS, 1× Glutamine).

After overnight recovery, medium was replaced with fresh 3T3 growth medium with or without addition of 19 Units/ml of recombinant human erythropoietin (rHuEpo) and left overnight again. Culture medium supernatants were collected and cleared of cells and debris either by centrifugation at 15K rpm for 10 minutes (without filtration) or by filtration (0.45 micron spin filter, 10 minutes, 15K rpm). Cleared supernatants were heated at 65° C. for 1 hour and mixed with an equal volume of 2× phosphatase reaction buffer containing 2M diethanolamine, 1 mM $MgCl_2$, 20 mM homoarginine, 1 mg/ml BSA (pre-heated by itself for 1 hour at 65° C. and then added), and 0.2 mM 4-methylumbelliferyl phosphate dicyclohexylammonium trihydrate in water. Reactions were allowed to proceed overnight at 37° C. and production of 4-methylumbelliferyl as a measure of phosphatase activity was measured at 360 nm/460 nm (excitation/emission wavelength). Results are shown in Table 1 below.

TABLE 1

| | −EPO | | | +EPO | | | fold stimulation |
|---|---|---|---|---|---|---|---|
| | − filtration | + filtration | average − baseline[1] | − filtration | + filtration | average − baseline | (avg +EPO / avg −EPO) |
| 1 9X-RS-pGTPLAP | 30 | 24 | 12 | 30 | 26 | 13 | 1.0 |
| 2 9X-RS-pGTPLAP/EPOR | 24 | 23 | 9 | 33 | 35 | 19 | 2.0 |
| 3 9X-RS-pGTPLAP/ EPOR/STAT5b | 69 | 62 | 51 | 169 | 154 | 147 | 2.9 |
| 4 12X-RS-Pgtplap | 34 | 34 | 19 | 47 | 46 | 32 | 1.7 |
| 5 12X-RS-pGTPLAP/EPOR | 32 | 32 | 17 | 45 | 42 | 29 | 1.7 |
| 6 12X-RS-pGTPLAP/ EPOR/STAT5b | 110 | 102 | 91 | 200 | 183 | 177 | 2.0 |
| 7 EPOR | 15 | 16 | | 16 | 14 | | |
| 8 STAT5b | 17 | 16 | | 14 | 14 | | |
| 9 nontransfected NIH3T3 | 13 | 14 | | 17 | 17 | | |

[1]"average − baseline" equals the average ( − filtration and + filtration) in the presence of a pGTPLAP less the approximate average of all samples in the absence of a pGTPLAP. Thus, the baseline used for both +EPO and −EPO was 15.
RS = response element repeat sequence

Example 3

Testing with IL-3 pGTPLAP DNAs with increasing copy numbers of response element triple repeat sequence were individually purified and linearized with ApaL1 for electroporation (263-269 V/12.8-17.6 microF pulse; BTX Electro Cell Manipulator 600) into BaF3 cells which express endogenous IL-3 receptors. Stable transfectants were selected for the presence of the Neomycin resistance gene (present in pGTPLAP) by a 2-week culture in standard culture medium (IMDM, 10% FetalClonell, 5×10e-5M beta-mercaptoethanol, 1× Glutamine, 2.5 ng/ml rMuIL-3 (Biosource)) supplemented with G418 (750 microgram/ml).

To measure cytokine-induced PLAP expression, cells were washed and re-plated in phenolred-free RPMI containing 0.2% BSA, 5×10e-5M beta-mercaptoethanol, 1× Glutamine at 10e6 cells/0.5 ml/well and incubated overnight at 37° C. Also, nontransfected BaF3 cells were used. One of every two wells per construct was supplemented with 25 ng/ml recombinant murine interleukin-3 (rMuIL-3) during the overnight incubation. Cell viability was assessed by Trypan Blue exclusion and culture medium supernatants were collected and cleared of cells and debris either by centrifugation at 15K rpm for 10 minutes (without filtration) or by filtration (0.45 micron spin filter, 10 minutes, 15K rpm). Cleared supernatants were heated at 65° C. for 1 hour and mixed with an equal volume of 2× phosphatase reaction buffer containing 2M diethanolamine, 1 mM MgCL2, 20 mM homoarginine, 1 mg/ml BSA (pre-heated by itself for 1 hour at 65° C. and then added), and 0.2 mM 4-methylumbelliferyl phosphate dicyclohexylammonium trihydrate (4-MUP) in water. Reactions were allowed to proceed overnight at 37° C. and production of 4-MU as a measure of phosphatase activity was measured at 360 nM/460 nM (excitation/emission wavelength). The results are shown in Table 2 below.

CGTCATTTCCAGGAAATCA CCGTCATTTCCAG-GAAATCA CCGTCATTTCCAGGAAATCA CCG CCGTA CCGTCATTTCCAGGAAATCA CCGTCATTTCCAG-GAAATCA CCGTCATTTCCAGGAAATCA CCGCCGTA CCGTCATTTCCAGGAAATCA CCGTCATTTCCAG-GAAATCA CCGTCATTTCCAGGAAATCA CCG CGGTCCCAGGTCCACTTCGCATATTAAG-GTGACGCGTGTGGCCTCGAACACC AAGCT (SEQ ID NO: 40)

was cloned into plasmid pGL3 basic (Promega) cut with KpnI and NheI (XbaI and NheI have compatible ends) to produce pGL3 basic containing a 9× response element repeat sequence and the TK promoter.

pGL3 hygro was produced by cloning a hygromycin B resistance gene into the BamHI site of the pGL3-promoter vector (Promega). A DNA fragment containing the 9× response element repeat sequence and TK promoter was released from the pGL basic3 vector by digestion with KpnI and HindIII. The DNA fragment was then ligated into pGL3 hygro cut with KpnI and HindIII to produce the reporter nucleic acid construct.

To generate the pool population of HuG-CSFR-luc cells, a clonal population of 32D HuG-CSFR ck3 cells was used. This cell line expresses the full-length human G-CSF receptor. The parental cell line 32D cl3 is now available at ATCC (ATCC No. CRL-11346, ATCC Name "32D clone 3"). The parental 32D cl3 cells were transfected with the cDNA for the human GCSF receptor. The sequence for human GCSF receptor is M59818.GB_PR1 (GenBane®). The vector used to express this cDNA is called pLJ, see Korman, Alan J., Frantz, J. Daniel, Strominger, Jack L., and Mulligan, Richard C., PNAS, 84:2150-2154 (1987). These cells were grown in RPMI 1640, supplemented with 10% Fetal Bovine Serum, 10 ng/mL murine IL-3 (mIL-3). A commercial source of mIL-3 is available from Biosource.

TABLE 2

| | −IL-3 | | | +IL-3 | | | fold stimulation |
|---|---|---|---|---|---|---|---|
| | − filtration | + filtration | average − baseline[1] | − filtration | + filtration | average − baseline | (avg +IL-3 / avg −IL-3) |
| nontransfected BaF3 cells | 16 | 14 | | 17 | 15 | | |
| 3X-RS- pGTPLAP | 35 | 33 | 20 | 85 | 82 | 70 | 3.5 |
| 6X-RS- pGTPLAP | 44 | 45 | 30 | 175 | 177 | 160 | 5.4 |
| 9X-RS- pGTPLAP | 53 | 54 | 40 | 276 | 257 | 250 | 6.2 |
| 12X-RS- pGTPLAP | 59 | 63 | 45 | 402 | 384 | 375 | 8.4 |
| Greater than 12X-RS- pGTPLAP | 48 | 48 | 33 | 384 | 389 | 370 | 11.2 |

[1]"average − baseline" equals the average (− filtration and + filtration) in the presence of a pGTPLAP less the approximate average (− filtration and + filtration) for all untransfected BaF3 cell samples. Thus, the baseline used for both +IL-3 and −IL-3 was 15. (The average baseline numbers in this table are rounded.)
RS = response element triple repeat sequence

Example 4

Making HuG-CSFR-luc Cell Line

To generate the reporter nucleic acid construct, a DNA fragment containing the 9× response element repeat sequence and the thymidine kinase promoter was removed from pGTPLAP by digesting with KpnI and XbaI. After removal, a fragment with the following sequence (the complementary strand will have both 5' and 3' overhangs resulting from the digestion):

To transfect the 32D HuG-CSFR ck3 cells with the reporter nucleic acid construct, 30 μg of reporter nucleic acid construct was electroporated into 1×10$^7$ 32D HuG-CSFR ck3 cells in a 4 mm cuvette at capacitance 500 μF, 300V using an Electro Cell Manipulator EDM 600 (BTX). Cells were incubated in nonselective medium overnight, then transferred into selective medium (RPMI 1640, 10% Fetal Bovine Serum, 10 ng/mL mIL-3, and 900 μg/mL Hygromycin B. Cells were plated at a density of approximately 4.1E5/well/mL in each well of a 24 well plate and left undisturbed for 2 weeks.

Actively growing colonies were pooled and divided into the wells of a six-well dish and then passaged in selective medium for two weeks.

Single cell clones were established by limiting dilution in selective medium and clonal populations were individually tested for G-CSF responsiveness. Specifically, clonal populations were incubated for four hours with 0.8 ng/mL and 5.0 ng/mL GCSF. Best responders were identified based on luminescence output-fold stimulation over background (assay medium alone). One such population of cells, which showed a three-fold stimulation over background, was chosen and designated as HuG-CSFR-luc (clone 40) cells. This is a cloned, stably transfected cell line.

Example 5

Making UT7/9X Cell Line

To generate the reporter gene construct, a DNA fragment containing the 9× response element repeat sequence was removed from pGTPLAP by digestion with KpnI and SacII. The DNA fragment had the sequence (both the strand shown and the complementary strand will have 3' overhangs resulting from the digestion):

CGTCATTTCCAGGAAATCA CCGTCATTTCCAG-GAAATCA CCGTCATTTCCAGGAAATCA CCG CCGTA CCGTCATTTCCAGGAAATCA CCGTCATTTCCAG-GAAATCA CCGTCATTTCCAGGAAATCA CCGCCGTA CCGTCATTTCCAGGAAATCA CCGTCATTTCCAG-GAAATCA CCGTCATTTCCAGGAAATCA CCGC (SEQ ID NO: 41).

A linker comprising SacII, NheI, SmaI, XhoI, and BglII sites was synthesized. A three-way ligation reaction was performed, comprised of the linker, the fragment containing the 9× response element repeat sequence, and pGL3 hygro that was cut with KpnI and BglII. This reaction served to ligate the linker and the fragment containing the 9× response element repeat sequence into the pGL3 hygro. pGL3 hygro, which contains the SV40 promoter, is described in Example 4 above. The resulting reporter nucleic acid construct was named pGL3 hygro 9× only #1.

To generate the pool population of UT7/9X cells, 1×10$^7$ UT7/EPO cells (Komatsu, N. et al. (1993) *Blood* 82: 456-464) grown in IMDM supplemented with 10% Fetal Bovine Serum (heat inactivated) and 1 U/mL of rHuEPO were transfected by electroporation with 30 µg of pGL3 hygro 9× only #1 in a 4 mm cuvette at capacitance 500 µF, 300V using an Electro Cell Manipulator ECM 600 (BTX). Cells were incubated in nonselective medium overnight, then passaged into selection medium (IMDM, 10% Fetal Bovine Serum, 1 U/mL rHuEPO, and 500 µg/mL Hygromycin B). Cells were plated and left undisturbed for 2 weeks. Actively growing colonies were then pooled and passaged into plates. Single cell clones were established by limiting dilutions. Clonal populations were individually tested for EPO responsiveness. Specifically, clonal populations were incubated with three different concentrations of rHuEPO (0.1, 1, and 3 U/mL). In the initial evaluation, best responders were selected based on a ≧4 fold luminescence output fold stimulation over background (assay medium alone). For the final selection of the clonal cell line, a full dose response curve was performed using Aranesp™ (range 200-0.01 ng/mL).

One such population of cells was chosen and designated as UT7/9X#6 cells. UT7/9X#6 was selected based on demonstrating the highest fold stimulation over the linear range of sensitivity of Aranesp™ (5 fold) and the lowest background. This is a cloned, stably transfected cell line.

Example 6

Determining In Vitro Potency of Recombinant Human Erythropoietin (rHuEPO)

Wash UT7/9X cells with PBS twice. Resuspend cells in Assay Medium (247.5 mL RPMI 1640 1× liquid with GlutaMAXT™ and HEPES buffer, with phenol red, 247.5 mL RPMI 1640 1× liquid without phenol red, 5 mL Fetal Bovine Serum, filter through a 0.22 µm filter unit) to a concentration of approximately 4.0 E+05 cells/mL and transfer to a horizontally positioned flask in a humidified incubator. Incubate at 37±2° C. and 5±1% for 17-24 hours. Following this incubation, determine cell concentration and percent cell viability. Viability should be ≧75%. In a 50 mL conical tube, prepare a cell suspension from this cell preparation in Assay Medium to a final concentration of 2 E+05 cells/mL. Mix well.

Dilute recombinant human Epo (rHuEPO) standard to approximately 40 ng/mL (4.8 U/mL) in Assay Medium (final concentration in wells will be 20 ng/mL, 2.4 U/mL). Make 9 serial dilutions (1:2 is suggested) in Assay Medium to create a 10 point dose response curve. It is suggested to perform replicates of three for each dilution tested.

Add 25 µL of UT7/9XGAS cells that are prepared as described in the first paragraph of Example 6 above to wells containing either 25 µL of standard or test sample. Wells to determine background contain 25 µL of UT7/9XGAS cells with 25 µL of Assay Media. Cells are mixed frequently in reagent reservoir to ensure uniformity when adding to assay plates. Final cell concentration is approximately 5,000 cells/well.

Media Only wells are also created that contained only 50 µL of Assay Media, containing neither rHuEPO nor cells. Plates are shaken and then incubated for 4±0.5 hours in the humidified incubator at 37±2° C. and 5±1% CO$_2$. Plates are removed and are allowed to come to room temperature without the lid for a minimum of ten minutes, not to exceed twenty minutes.

Steady-Glo™ Luciferase Assay System (Promega #E2520) is used in accordance with instructions. Add 50 µL of Steady-Glo™ to each well of assay plates, including Media Only wells. Plates are covered to minimize light exposure. Plates are shaken on plate shaker for a minimum of 5 minutes. Plates are then incubated at room temperature for 10 minutes to 2 hours. Alternatively, the plates may be left on the shaker for this incubation period.

Plates are read in a Luminometer TopCount NXT™ Microplate Scintillation and Luminescence Counter (Packard/Perkin Elmer). Allow the plates to adapt in the dark for at least 1 minute before reading. Read luminescence for a minimum of 1 second per well. Import luminescence values into Excel or similar software package. Plot relative luminescence units versus log dose concentration. Calculate effective concentration 50 (EC50) for standard and test samples.

Other embodiments of the invention will be apparent to those skilled in the art from consideration of the specification and practice of the invention disclosed herein.

We claim:

1. An isolated nucleic acid comprising a response element region comprising: (i) the sequence GTCATTTCCAGGAAATCACC (SEQ ID NO: 1) or (ii) a sequence complementary to the sequence in (i).

2. An isolated nucleic acid comprising a response element region comprising:
(a) (i) the sequence GTCATTTCCAGGAAATCACCGTCATTTCCAGGAAA TCACCGTCATTTCCAGGAAATCACC (SEQ ID NO: 2) or (ii) a sequence complementary to the sequence in (i);
(b) (i) the sequence GTCATTTCCAGGAAATCACCGTCATTTCCAGGAAA TCACCGTCATTTCCAGGAAATCACC-Y-GTCATTTCCAGGAAATCACCG TCATTTCCAGGAAATCACCGTCATTTCCAGGAAATCACC (SEQ ID NO: 3) or (ii) a sequence complementary to the sequence in (i);
(c) (i) the sequence GTCATTTCCAGGAAATCACCGTCATTTCCAGGAAA TCACCGTCATTTCCAGGAAATCACC-Y-GTCATTTCCAGGAAATCACCG TCATTTCCAGGAAATCACCGTCATTTCCAGGAAATCACC-X-GTCATTT CCAGGAAATCACCGTCATTTCCAGGAAATCACCGT-CATTTCCAGGAAATC ACC (SEQ ID NO: 4) or (ii) a sequence complementary to the sequence in (i); or
(d) (i) the sequence GTCATTTCCAGGAAATCACCGT-CATTTCCAGGAAA TCACCGTCATTTCCAG-GAAATCACC-Y-GTCATTTCCAGGAAATCACCG TCATTTCCAGGAAATCACCGTCATTTC-CAGGAAATCACC-X-GTCATTT CCAGGAAAT-CACCGTCATTTCCAGGAAATCACCGT-CATTTCCAGGAAATC ACC-Z-GTCATTTCCAGGAAATCACCGTCATTTCCAGG-AAATCACCG TCATTTCCAGGAAATCACC (SEQ ID NO: 5) or (ii) a sequence complementary to the sequence in (i);
wherein Y, X, and Z are each independently selected from a nucleic acid sequence of 0 to 23 nucleotides.

3. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAG-GAAATCACCGTCATTTCCAGGAAATCACC-X-GTCATTTCCAGG AAATCACCGTCATTTCCAGGAAATCAC-CGTCATTTCCAGGAAATCACC-Z-GTCATTTC-CAGGAAATCACCGTCATTTCCAGGAAAT-CACCGTCATTTCCAGG AAATCACC (SEQ ID NO: 9)

wherein Y, X, and Z are each a nucleic acid sequence of 0 nucleotides.

4. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAGGAAATCACCGTCATTTCCAGGAAATCACC-X-GTCATTTCCAGG AAATCACCGTCATTTCCAGGAAATCAC-CGTCATTTCCAGGAAATCACC-Z-GTCATTTC-CAGGAAATCACCGTCATTTCCAGGAAAT-CACCGTCATTTCCAGG AAATCACC (SEQ ID NO: 10)
wherein Y, X, and Z are each a nucleic acid sequence of 8 nucleotides.

5. The isolated nucleic acid of claim 4, wherein Y, X, and Z are each the nucleic acid sequence GCCGTACC.

6. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAGGAAATCACCGTCATTTCCAGGAAATCACC-X-GTCATTTCCAGG AAATCACCGTCATTTCCAGGAAATCAC-CGTCATTTCCAGGAAATCACC-Z-GTCATTTC-CAGGAAATCACCGTCATTTCCAGGAAAT-CACCGTCATTTCCAGG AAATCACC (SEQ ID NO: 12)
wherein Y is a nucleic acid sequence of 8 nucleotides, X is a nucleic acid sequence of 10 nucleotides, and Z is a nucleic acid sequence of 16 nucleotides.

7. The isolated nucleic acid of claim 6, wherein Y is the nucleic acid sequence GCCGTACC, X is the nucleic acid sequence TACCGGTCTG (SEQ ID NO 14), and Z is the nucleic acid sequence ACCGGCCTAGTGCGTC (SEQ ID NO: 15).

8. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAGGAAATCACCGTCATTTCCAGGAAATCACC-X-GTCATTTCCAGG AAATCACCGTCATTTCCAGGAAATCAC-CGTCATTTCCAGGAAATCACC (SEQ ID NO: 16)
wherein Y and X are each a nucleic acid sequence of 0 nucleotides.

9. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAGGAAATCACCGTCATTTCCAGGAAATCACC-X-GTCATTTCCAGG AAATCACCGTCATTTCCAGGAAATCAC-CGTCATTTCCAGGAAATCACC (SEQ ID NO: 17)
wherein Y and X are each a nucleic acid sequence of 8 nucleotides.

10. The isolated nucleic acid of claim 9, wherein Y and X are each the nucleic acid sequence GCCGTACC.

11. The isolated nucleic acid of claim 2, comprising the sequence:
GTCATTTCCAGGAAATCACCGTCATTTC-CAGGAAATCACCGT CATTTCCAGGAAATCACC-Y-GTCATTTCCAGGAAATCACCGTCATTT CCAGGAAATCACCGTCATTTCCAGGAAATCACC-X-GTCATTTCCAGG AAATCACCGTCATTTCCAGGAAATCAC-CGTCATTTCCAGGAAATCACC (SEQ ID NO: 19)
wherein Y is a nucleic acid sequence of 8 nucleotides and X is a nucleic acid sequence of 10 nucleotides.

12. The isolated nucleic acid of claim 11, wherein Y is the nucleic acid sequence GCCGTACC and X is the nucleic acid sequence TACCGGTCTG (SEQ ID NO: 14).

13. The isolated nucleic acid of claim 2, wherein Y, X, and/or Z are independently selected from a sequence that is capable of binding to at least one transcription factor selected from NFAT, AP-1, CRE, NFκB, and a member of the STAT protein family.

14. A response element region comprising more than one response element sequences comprising the sequence GTCATTTCCAGGAAATCACC (SEQ ID NO: 1) wherein the center region of at least two response element sequences are spatially oriented to be in the same location (on the y and z axis) plus or minus 36 degrees, relative to the center axis of the double-helical DNA (x-axis), wherein the center region is the tenth and eleventh nucleotides AG of the sequence GTCATTTCCAGGAAATCACC (SEQ ID NO: 1).

15. A response element region comprising at least two series of more than one response element sequences comprising the sequence GTCATTTCCAGGAAATCACC (SEQ ID NO: 1);
wherein each series of more than one response element sequences are linked together by a sequence of approximately eight nucleotides,
wherein, within a first series of the response element sequences, each center region of the response element sequences are spatially oriented to be in approximately the same location (on the y and z axis) plus or minus 36 degrees, relative to the center axis of the double-helical DNA (x-axis), wherein the center region is the tenth and eleventh nucleotides AG of the sequence GTCATTTC-CAGGAAATCACC (SEQ ID NO: 1);
wherein, within a second series of the response element sequences, each center region of the response element sequences are spatially oriented to be in approximately the same location (on the y and z axis) plus or minus 36 degrees, relative to the center axis of the double-helical DNA (x-axis), wherein the center region is the tenth and eleventh nucleotides AG of the sequence GTCATTTC-CAGGAAATCACC (SEQ ID NO: 1); and
wherein the center region of the response element sequences of the second series of the response element sequences are spatially oriented to be approximately 72 to 86 degrees from the center region of the first series of the response element sequences as determined from the y and z axis relative to the center axis of the double-helical DNA as the x axis.

16. A response element region comprising at least two series of more than one response element sequences comprising the sequence GTCATTTCCAGGAAATCACC (SEQ ID NO: 1);
wherein each series of more than one response element sequences are linked together by a sequence of approximately eight nucleotides,
wherein, within a first series of the response element sequences, each center region of the response element sequences are spatially oriented to be in approximately the same location (on the y and z axis) plus or minus 36 degrees, relative to the center axis of the double-helical DNA (x-axis), wherein the center region is the tenth and eleventh nucleotides AG of the sequence GTCATTTC-CAGGAAATCACC (SEQ ID NO: 1);

wherein, within a second series of the response element sequences, each center region of the response element sequences are spatially oriented to be in approximately the same location (on the y and z axis) plus or minus 36 degrees, relative to the center axis of the double-helical DNA (x-axis), wherein the center region is the tenth and eleventh nucleotides AG of the sequence GTCATTTC-CAGGAAATCACC (SEQ ID NO: 1); and wherein the center region of the response element sequences of the second series of the response element sequences are spatially oriented to be approximately 144 to 180 degrees from the center region of the first series of the response element sequences as determined from the y and z axis relative to the center axis of the double-helical DNA as the x axis.

17. A vector comprising a promoter and nucleic acid comprising a response element region comprising (i) the sequence GTCATTTCCAGGAAATCACC (SEQ ID NO: 1) or (ii) a sequence complementary to the sequence in (i).

18. A vector comprising a promoter and nucleic acid comprising a response element region comprising:
(a) (i) the sequence GTCATTTCCAGGAAATCACCGT-CATTTCCAGGAAA TCACCGTCATTTCCAG-GAAATCACC (SEQ ID NO: 2) or (ii) a sequence complementary to the sequence in (i);
(b) (i) the sequence GTCATTTCCAGGAAATCACCGT-CATTTCCAGGAAA TCACCGTCATTTCCAG-GAAATCACC-Y-GTCATTTCCAGGAAATCACCG TCATTTCCAGGAAATCACCGTCATTTC-CAGGAAATCACC (SEQ ID NO: 3) or (ii) a sequence complementary to the sequence in (i);
(c) (i) the sequence GTCATTTCCAGGAAATCACCGT-CATTTCCAGGAAA TCACCGTCATTTCCAG-GAAATCACC-Y-GTCATTTCCAGGAAATCACCG TCATTTCCAGGAAATCACCGTCATTTC-CAGGAAATCACC-X-GTCATTT CCAGGAAAT-CACCGTCATTTCCAGGAAATCACCGT-CATTTCCAGGAAATC ACC (SEQ ID NO: 4) or (ii) a sequence complementary to the sequence in (i); or
(d) (i) the sequence GTCATTTCCAGGAAATCACCGT-CATTTCCAGGAAA TCACCGTCATTTCCAG-GAAATCACC-Y-GTCATTTCCAGGAAATCACCG TCATTTCCAGGAAATCACCGTCATTTC-CAGGAAATCACC-X-GTCATTT CCAGGAAAT-CACCGTCATTTCCAGGAAATCACCGT-CATTTCCAGGAAATC ACC-Z-GTCATTTCCAGGAAATCACCGTCATTTCCAGG-AAATCACCG TCATTTCCAGGAAATCACC (SEQ ID NO: 5) or (ii) a sequence complementary to the sequence in (i);

wherein Y, X, and Z are each independently selected from a nucleic acid sequence of 0 to 23 nucleotides.

19. The vector of claim 17 or 18, further comprising a reporter nucleic acid, wherein the response element region is operably linked to the promoter and the promoter is operably linked to the reporter nucleic acid.

20. The vector of claim 19, wherein the promoter is a thymidine kinase (TK) promoter and the reporter nucleic acid is a nucleic acid that encodes luciferase.

21. The vector of claim 19, wherein the promoter is a SV40 promoter and the reporter nucleic acid is a nucleic acid that encodes luciferase.

22. A host cell comprising a vector of claim 19.

23. The host cell of claim 22, wherein host cell is responsive to at least one signaling molecule selected from G-CSF, EPO, and IL-3.

24. The host cell of claim 23, wherein host cell is responsive to at least one signaling molecule selected from recombinant methionyl human granulocyte colony-stimulating factor, epoetin alfa, and darbepoetin alfa.

25. The host cell of claim 22, wherein the host cell is a signaling molecule-responsive host cell.

26. A method for determining the activity of a test composition comprising a signaling molecule, comprising
a) contacting the test composition with a signaling molecule-responsive host cell comprising the vector of claim 19 under conditions in which the reporter nucleic acid expresses a reporter protein in response to the signaling molecule; and
b) detecting the reporter protein to determine the activity of the test composition.

27. The method of claim 26, wherein the host cell is responsive to at least one signaling molecule selected from G-CSF-like molecule, erythropoietic product, and IL-3.

28. The method of claim 27, wherein the host cell is responsive to at least one signaling molecule selected from recombinant methionyl human granulocyte colony-stimulating factor, epoetin alfa, and darbepoetin alfa.

29. The method of claim 26, wherein the promoter is a TK promoter and the reporter nucleic acid encodes luciferase.

30. The method of claim 26, wherein the promoter is a SV40 promoter and the reporter nucleic acid encodes luciferase.

31. A method for determining the activity of a test composition comprising a signaling molecule, comprising
(a) contacting the test composition with a signaling molecule-responsive host cell comprising the vector of claim 19 under conditions in which the reporter nucleic acid expresses a reporter protein in response to the signaling molecule;
(b) detecting the reporter protein to determine the activity of the test composition;
(c) contacting a signaling molecule-responsive host cell comprising the vector of claim 19 with a blank composition that does not comprise a signaling molecule;
(d) detecting the reporter protein to determine the activity of the blank composition; and
(e) comparing the level of detected reporter protein expression in (b) with the level of detected reporter protein expression in (d).

32. The method of claim 31, wherein the promoter is a TK promoter and the reporter nucleic acid encodes luciferase.

33. The method of claim 31, wherein the promoter is a SV40 promoter and the reporter nucleic acid encodes luciferase.

34. A method for determining the activity of a test composition comprising a signaling molecule, comprising
(a) contacting the test composition with a signaling molecule-responsive host cell comprising the vector of claim 19 under conditions in which the reporter nucleic acid expresses a reporter protein in response to the signaling molecule;
(b) detecting the reporter protein to determine the activity of the test composition;
(c) contacting a signaling molecule-responsive host cell comprising the vector of claim 19 with a standard composition that comprises a signaling molecule;
(d) detecting the reporter protein to determine the activity of the standard composition; and (e) comparing the level of detected reporter protein expression in (b) with the level of detected reporter protein expression in (d).

35. The method of claim 34, wherein the promoter is a TK promoter and the reporter nucleic acid encodes luciferase.

36. The method of claim 34, wherein the promoter is a SV40 promoter and the reporter nucleic acid encodes luciferase.

37. A method of calculating a relative potency of a test composition, comprising
   (a) contacting the test composition with a signaling molecule-responsive host cell comprising the vector of claim 19 under conditions in which the reporter nucleic acid expresses a reporter protein in response to the signaling molecule;
   (b) detecting the reporter protein to determine the activity of the test composition;
   (c) making serial dilutions of a standard composition that comprises a signaling molecule at a known concentration;
   (d) separately contacting a signaling molecule-responsive host cell comprising the vector of claim 19 with each of the standard test compositions of (c);
   (e) detecting the reporter protein to determine the activity of each of the serial dilutions of the standard test composition; and
   (f) calculating the relative potency of the signaling molecule in the test sample by comparing the level of detected reporter protein expression in (b) to the levels of detected reporter protein expression in (e).

38. The method of claim 37, wherein the promoter is a TK promoter and the reporter nucleic acid encodes luciferase.

39. The method of claim 37, wherein the promoter is a SV40 promoter and the reporter nucleic acid encodes luciferase.

40. A method for determining whether a test compound has activity of a given signaling molecule, comprising
   a) contacting the test compound with a signaling molecule-responsive host cell comprising the vector of claim 19 under conditions in which the reporter nucleic acid expresses a reporter protein in response to compounds that have the activity of the given signaling molecule;
   b) detecting the reporter protein;
   c) comparing the level of detected reporter protein expression in (b) with the level of detected reporter protein expressed by a signaling molecule-responsive host cell comprising the vector of claim 19 in the absence of the test compound to determine whether the test compound has the activity of the given signaling molecule.

41. The method of claim 40, wherein the promoter is a TK promoter and the reporter nucleic acid encodes luciferase.

42. The method of claim 40, wherein the promoter is a SV40 promoter and the reporter nucleic acid encodes luciferase.

43. The method of claim 40, wherein the given signaling molecule is selected from G-CSF-like molecule, erythropoietic product, and IL-3.

44. The method of claim 43, wherein the given signaling molecule is selected from recombinant methionyl human granulocyte colony-stimulating factor, epoetin alfa, and darbepoetin alfa.

45. A method for determining whether a test compound has activity of a given signaling molecule, comprising
   a) contacting the test compound with a signaling molecule-responsive host cell comprising the vector of claim 19 under conditions in which the reporter nucleic acid expresses a reporter protein in response to compounds that have the activity of the given signaling molecule;
   b) detecting the reporter protein;
   c) comparing the level of detected reporter protein expression in (b) with the level of detected reporter protein expressed by a signaling molecule-responsive host cell comprising the vector of claim 19 in the presence of the given signaling molecule, but in the absence of the test compound, to determine whether the test compound has the activity of the given signaling molecule.

46. The method of claim 45, wherein the promoter is a TK promoter and the reporter nucleic acid encodes luciferase.

47. The method of claim 45, wherein the promoter is a SV40 promoter and the reporter nucleic acid encodes luciferase.

48. The method of claim 45, wherein the given signaling molecule is selected from G-CSF-like molecule, erythropoietic product, and IL-3.

49. The method of claim 48, wherein the given signaling molecule is selected from recombinant methionyl human granulocyte colony-stimulating factor, epoetin alfa, and darbepoetin alfa.

50. A method for determining whether a test compound impacts the activity of a signaling molecule, comprising
   a) contacting the test compound with a signaling molecule-responsive host cell comprising the vector of claim 19 in the presence of the signaling molecule under conditions in which the reporter nucleic acid expresses a reporter protein in response to the signaling molecule;
   b) detecting the reporter protein;
   c) comparing the level of detected reporter protein expression in (b) with the level of detected reporter protein expressed by a signaling molecule-responsive host cell comprising the vector of claim 19 in the presence of the signaling molecule, but in the absence of the test compound, to determine whether the test compound impacts the activity of the signaling molecule.

51. The method of claim 50, wherein the promoter is a TK promoter and the reporter nucleic acid encodes luciferase.

52. The method of claim 50, wherein the promoter is a SV40 promoter and the reporter nucleic acid encodes luciferase.

53. The method of claim 50, wherein host cell is responsive to at least one signaling molecule selected from G-CSF, EPO, and IL-3.

54. The method of claim 53, wherein host cell is responsive to at least one signaling molecule selected from G-CSF, epoetin alfa, and darbepoetin alfa.

55. A method of producing a polypeptide from an ex vivo mammalian system, comprising producing the polypeptide, testing the polypeptide with the host cell of claim 22, and determining the amount of protein produced and/or activity of the protein produced by the ex vivo system.

* * * * *